US007741029B2

(12) United States Patent
Schuh et al.

(10) Patent No.: US 7,741,029 B2
(45) Date of Patent: Jun. 22, 2010

(54) DIAGNOSIS AND TREATMENT OF BLOOD DISORDERS

(76) Inventors: Andre Schuh, 359 Blythwood Road, Toronto, Ontario (CA) M4N 1A7; Willem Ouwehand, 147 Hemingford Road, Islington, London, N1 1BZ (GB)

( * ) Notice: Subject to any disclaimer, the term of this patent is extended or adjusted under 35 U.S.C. 154(b) by 1341 days.

(21) Appl. No.: 10/471,327

(22) PCT Filed: Mar. 7, 2002

(86) PCT No.: PCT/CA02/00291

§ 371 (c)(1),
(2), (4) Date: Aug. 16, 2004

(87) PCT Pub. No.: WO02/070738

PCT Pub. Date: Sep. 12, 2002

(65) Prior Publication Data

US 2005/0069875 A1 Mar. 31, 2005

Related U.S. Application Data

(60) Provisional application No. 60/273,941, filed on Mar. 7, 2001.

(51) Int. Cl.
*C12Q 1/68* (2006.01)
*C12P 19/34* (2006.01)
(52) U.S. Cl. .......................... 435/6; 435/91.1; 435/91.2
(58) Field of Classification Search ................... None
See application file for complete search history.

(56) References Cited

U.S. PATENT DOCUMENTS 5,474,796 A * 12/1995 Brennan ................. 427/2.13

FOREIGN PATENT DOCUMENTS

| WO | WO 91 03557  |   | 3/1991  |
|----|--------------|---|---------|
| WO | WO 00/29448  | * | 5/2000  |
| WO | WO 02 070696 |   | 9/2002  |
| WO | WO 02 085942 |   | 10/2002 |

OTHER PUBLICATIONS

Ouwehand and Navarrete. Molecular Haematology. Provan and Gribben (Eds) Blackwell Science 2000. Chapter 14, pp. 182-197.*
Schuh et al. Blood, 2002, vol. 99, No. 5, pp. 1692-1698.*
H.M. DeLisser. "Epitope Mapping." Methods in Molecular Biology, vol. 96: Adhesion Protein Protocols, 1999, pp. 11-20.
C. Meier and J.W. Engels. "Peptide Nucleic Acids (PNAs)—Unusual Properties of Nonionic Oligonucleotide Analogues." Angew. Chem. Int. Ed. Engl. 1992, vol. 31, No. 8, pp. 1008-1010.
U. Englisch and D.H. Gauss. "Chemically Modified Oligonucleotides as Probes and Inhibitors." Angew. Chem. Int. Ed. Engl., vol. 30, No. 6, Jun. 1991, pp. 613-629.
F. Felici et al. "Peptide and protein display on the surface of filamentous bacteriophage." Biotechnology Annual Review, vol. 1, 1995, pp. 149-183.
W. Gish and D.J. States. "Identification of protein coding regions by database similarity search." Nature Genetics, vol. 3, Mar. 1993, pp. 266-272.
E.S. Kawasaki. "Amplification of RNA." PCR Protocols: A guide to Methods and Applications, Academic Press Inc., 1990, pp. 21-27.
T.L. Madden et al. "Network BLAST Server Applications." Methods in Enzymology, vol. 266 (1996) pp. 131-141.
B.A. Morgan and J.A. Gainor. "Approaches to the Discovery of Non-Peptide Ligands for Peptide Receptors and Peptidases." Annual Reports in Medicinal Chemistry, Section VI—Topics in Chemistry and Drug Design, Chapter 26, 1989, pp. 243-252.
U. Reineke et al. "Antigen Sequence- and Library-Based Mapping of Linear and Discontinuous Protein-Protein-Interaction Sites by Spot Synthesis." Current Topics in Microbiology and Immunology, 243 (1999), pp. 23-36.
A.C. Schuh et al. "Cell Surface Antigen CD109 Is a Novel Member of the a2 Macroglobulin/C3, C4, C5 Family of Thioester Containing Proteins." Blood 98 (11):50b (2001).
R. Steen and T. Egeland. "CD34 Molecule Epitope Distribution on Cells of Haematopoietic Origin." Leukemia and Lymphoma, 1998, vol. 30, pp. 23-30.
D.R. Sutherland and E.L. Yeo. "CDw109 Cluster report." Leukocyte Typing V (Schlossman S. et al eds.), Oxford University Press, Oxford, pp. 1767-1769, 1995.
B. Westerlund-Wikstorm. "Peptide display on bacterial flagella: Principles and applications." Int. J. Med. Microbiol., 290, pp. 223-230 (2000).
Database EMBL Online, Feb. 2, 2001. "Hydrophobic domain protein isolated from HT-1080 cells." retrieved from EBI Database accession No. AAB12127.
J.F. Yu et al. "Comparison of the expression of CD109 and CD135 on CD34+ cells in human marrow, cord blood, and peripheral blood." Blood, vol. 94, No. 10, Suppl. 1, Part 2, Nov. 1999, p. 136b.
Database EMBL 'Online, Feb 2, 2001. "Hydrophobic domain protein cDNA HP02837 isolated from HT-1080 cells." Retrieved from EBI, Database accession No. AAA62010.

(Continued)

*Primary Examiner*—Juliet C Switzer
(74) *Attorney, Agent, or Firm*—Ballard Spahr LLP

(57) ABSTRACT

Based on the discovery of the nucleotide and amino acid differences which distinguish the Gov$^a$ and Gov$^b$ allelic forms of the membrane glycoprotein CD109, and which comprise the biallelic Gov platelet alloantigen system, compositions and methods are provided for determining the Gov genotype and phenotype of individuals. Also provided, on the basis of this discovery, are compositions and methods for treating disorders associated with Gov alloantigen incompatibility, such as the bleeding disorders post-transfusion purpura, post-transfusion platelet refractoriness, and neonatal alloimmune thrombocytopenia. The two allelic forms of CD109 differ by a single amino acid. The Gov$^a$ allelic form has Tyr at amino acid position 703 in the CD109 sequence. The Gov$^b$ allelic form has Ser at the same position. This amino acid difference is due to a single change, from A for the Gov$^a$ allele to C for the Gov$^b$ allele, in the CD109 gene.

20 Claims, No Drawings

OTHER PUBLICATIONS

S.F. Altschul et al. "Basic Local Alignment Search Tool." J. Mol. Biol. (1990) 215, pp. 403-410.

S.F. Altschul et al. "Gapped BLAST and PSI-BLAST: a new generation of protein database search programs." Nucleic Acids Research, 1997, vol. 25, No. 17, pp. 3389-3402.

D. R. Burton. "Commentary Phage Display." Immunotechnology 1, (1995), pp. 87-94.

R. Cortese et al. "Selection of biologically active peptides by phage display of random peptide libraries." Current Opinion in Biotechnology, 1996, vol. 7, pp. 616-621.

J. M. Gershoni et al. "Combinatorial libraries, epitope structure and the prediction of protein conformation." Immunology Today, Mar. 1997, vol. 18, Issue 3, pp. 108-110.

J. Goodchild. "Conjugates of Oligonucleotides and Modified Oligonucleotides: A Review of Their Synthesis and Properties." Bioconjugate Chemistry, May/Jun. 1990, vol. 1, No. 3, pp. 165-187.

E. Lesnik et al. "Oligodeoxynucleotides Containing 2'-O-Modified Adenosine: Synthesis and Effects on Stability of DNA:RNA Duplexes." Biochemistry, 1993, vol. 32, No. 30, pp. 7832-7838.

J. Tseng-Law et al. "Identification of a peptide directed against the anti-CD34 antibody, 9C5, by phage display and its use in hematopoietic stem cell selection." Experimental Hematology, 1999, vol. 27, 936-945.

J. Van de Water et al. "Detection of Molecular Determinants and Epitope Mapping Using Maldi-TOF Mass Spectrometry." Clinical Immunology and Immunopathology, vol. 85, No. 3, Dec. 1997, pp. 229-235.

M. H. V. Van Regenmortel et al. "Measurement of antigen-antibody interactions with biosensors." Journal of Molecular Recognition, 1998, vol. 11, pp. 163-167.

J. Zhang and T. L. Madden. PowerBLAST: A New Network BLAST Application for Interactive or Automated Sequence Analysis and Annotation. Genone Research, 1997, pp. 649-656.

J.O. Bordin et al. "Maternal immunization to Gov system alloantigens on human platelets." Transfusion, vol. 37, No. 8, Aug. 1997, pp. 823-828.

R.W.A.M. Kuijpers et al. "$NH_2$-Terminal Globular Domain of Human Platelet Glycoprotein Ibα Has a Methionine$^{145}$/Threonine$^{145}$ Amino Acid Polymorphism, Which Is Associated with the HPA-2 (Ko) Alloantigens." J. Clin. Invest., vol. 89, Feb. 1992, pp. 381-384.

T. Nakatani et al. "Functional Expression of Human Monoclonal Antibody Genes Directed Against Pseudomonal Exotoxin A in Mouse Myeloma Cells." Bio/Technology, vol. 7, Aug. 1989, pp. 805-810.

P.J. Newman et al. "Enzymatic Amplification of Platelet-specific Messenger RNA Using the Polymerase Chain Reaction." J. Clin. Invest., vol. 82, Aug. 1998, pp. 739-743.

P.J. Newman et al. "The Human Platelet Alloantigens, Pl$^{A1}$ and Pl$^{A2}$, Are Associated with a Leucine$^{33}$/Proline$^{33}$ Amino Acid Polymorphism in Membrane Glycoprotein IIIa, and Are Distinguishable by DNA Typing." J. Clin. Invest., vol. 83, May 1989, pp. 1778-1781.

P.E. Nielsen et al. "Peptide nucleic acids (PNAs): Potential anti-sense and anti-gene agents." Anti-Cancer Drug Design (1993), 8, pp. 53-63.

W. Ouwehand & C. Navarrete. "The molecular basis of blood cell alloantigens." Molecular Haematology, Provan and Gribben (Eds), Blackwell Science (2000), Chapter 14, pp. 182-197.

D.R. Sutherland et al. "Identification of a Cell-Surface Antigen Associated With Activated T. Lymphoblasts and Activated Platelets." Blood, vol. 77, No. 1 (Jan. 1, 1991), pp. 84-93.

R. Wang et al. "An Amino Acid Polymorphism within the RGD Binding Domain of Platelet Membrane Glycoprotein IIIa Is Responsible for the Formation of the Pen$^a$/Pen$^b$ Alloantigen System." J. Clin. Invest., vol. 90, Nov. 1992, pp. 2038-2043.

E.S. Ward et al. "Binding activities of a repertoire of single immunoglobulin variable domains secreted from *Escherichia coli*." Nature, vol. 341, Oct. 12, 1989, pp. 544-546.

J.W. Smith et al. "Investigation of human platelet alloantigens and glycoproteins using non-radioactive immunoprecipitation." Journal of Immunological Methods, vol. 158, No. 1, 1993, pp. 77-85.

J.W. Smith et al. "Characterization and localization of the Gov$^{a/b}$ alloantigens to the Glycosylphosphatidylinositol-Anchored Protein CDW109 on Human Platelets." Blood, vol. 86, No. 7, Oct. 1995, pp. 2807-2814.

J.E. Berry et al. "Detection of Gov system antibodies by MAIPA reveals an immunogenicity similar to the HPA-5 alloantigens." Brtish Journal of Haematology, vol. 110, No. 3, Sep. 2000, pp. 735-742.

J.G. Kelton et al. "Gov$^{a/b}$ Alloantigen System on Human Platelets." Blood, vol. 75, No. 11, Jun. 1990, pp. 2172-2176.

S. Lyman et al. "Polymorphism of Human Platelet Membrane Glycoprotein IIb Associated With the Bak$^a$/Bak$^b$ Alloantigen System." Blood, vol. 75, No. 12, Jun. 1990, pp. 2343-2348.

J.G. Kelton et al. "ABH antigens on human platelets: Expression on the glycosyl phosphatidylinositol-anchored protein CD109." Journal of Laboratory and Clinical Medicine, vol. 132, No. 2, Aug. 1998, pp. 142-148.

A.C. Schuh et al. "A tyrosine703serine polmorphism of CD109 defines the Gov platelet alloantigens." Blood, vol. 99, No. 5, Mar. 2002, pp. 1692-1698.

M. Lin et al. "Cell surface antigen CD109 is a novel member of the alpha2 macroglobulin/C3, C4, C5 family thioester-containing protein." Blood, vol. 99, No. 5, Mar. 2002, pp. 1683-1691.

Suciu-Foca N, Reed E, Rubinstein P, MacKenzie W, Ng AK, King DW. A late-differentiation antigen associated with the helper inducer function of human T cells. Nature. 1985;318:465-467.

Brashem-Stein C, Nugent D, Bernstein ID. Characterization of an antigen expressed on activated human T cells and platelets. J Immunol. 1988; 140:2330-2333.

Haregewoin A, Solomon K, Hom RC, et al. Cellular expression of a GPI-linked T cell activation protein. Cell Immunol. 1994;156:357-370.

Solomon KR, Mallory MA, Finberg RW. Determination of the non-ionic detergent insolubility and phosphoprotein associations of glycosylphosphatidylinositol-anchored proteins expressed on T cells. Biochem J. 1998;334:325-333.

Totty NF, Waterfield MD, Hsuan JJ. Accelerated high-sensitivity microsequencing of proteins and peptides using a miniature reaction cartridge. Protein Sci. 1992;1:1215-1224.

Murray LJ, Bruno E, Uchida N, et al. CD109 is expressed on a subpopulation of CD34+ cells enriched in hematopoietic stem and progenitor cells. Exp Hematol. 1999;27:1282-1294.

* cited by examiner

DIAGNOSIS AND TREATMENT OF BLOOD DISORDERS

CROSS-REFERENCE TO RELATED APPLICATIONS

This application is a National Stage application based on International Application No. PCT/CA02/00291, filed Mar. 7, 2002, which claims priority to U.S. Provisional Application No. 60/273,941, filed Mar. 7, 2001.

FIELD OF THE INVENTION

The present invention provides novel compositions and methods for use in diagnosing the occurrence of certain serious disorders, especially certain bleeding disorders, and novel compositions and methods for use in treating such a disorder, in a person in which the disorder has occurred, and novel compositions and methods for use in avoiding such a disorder, in an individual who is susceptible thereto.

BACKGROUND OF THE INVENTION

Among the disorders, which the invention concerns, are those involving abnormal and excessive bleeding due to destruction of blood platelets ("platelets").

These disorders include, but are not restricted to, post-transfusion purpura ("PTP") and post-transfusion platelet refractoriness ("PTPR"), which are suffered by some persons who receive blood, platelets, leukocyte concentrates, or plasma from other persons by transfusion or the like.

The disorders also include one that is suffered by fetuses and newborns and is known as "neonatal alloimmune thrombocytopenia" ("NATP"). This disorder can cause death of fetuses and serious birth defects or death of newborns. NATP is estimated to affect about 1 in 1000 newborns. In NATP, fetal platelets, which enter the mother's blood stream, induce production in the mother of antibodies directed against fetal platelets. These maternal antibodies then pass with the mother's blood into the fetus and mediate destruction of platelets in the fetus.

A mother, whose fetus or newborn suffers from NATP, is at increased risk of suffering PTP or PTPR.

When platelets from a first human (a "donor") are introduced into the blood system of a second human (a "recipient") by transfusion, through the placenta (in the case of fetal blood entering the mother), or the like, the recipient may mount an immune response against the platelets from the donor. Such an immune response is referred to as an "alloimmune" response, because it involves antibodies reacting-against antigens of a different individual of the same species. The alloimmune response to platelets is due to an immune response of the recipient against "alloantigens" (antigens of the same species as that mounting the immune response) on platelets from the donor. These alloantigens are found on membrane glycoproteins that occur in the cell membranes, which define the outer surfaces of platelets ("platelet membranes"). In this invention, the glycoprotein is anchored to the membrane in an atypical manner through an anchor consisting of glycosylphosphatidylinositol (GPI), which anchors an extracellular domain or segment of the glycoprotein exposed to the outside of the platelet. It is thought that alloantibodies, which are generated in an alloimmune response against platelet alloantigens, interact with the extracellular domains of the alloantigens.

The platelet alloantigens that a person has are determined by the person's genetics. A donor, because of his or her genetics, may have a platelet alloantigen, which a recipient, who receives blood, platelets, leukocytes or plasma from the donor, does not have, because of the recipient's genetics. In such a situation, the immune system of the recipient may recognize the donor's alloantigen as "non-self," and raise an immune response against, the platelet alloantigen, which the donor has but the recipient does not.

Membrane glycoprotein alloantigens have been characterised for both human red blood cells and human platelets. It is noteworthy, however, that they also occur on other cell types, such as leukocytes and endothelial cells, where they may also occasion various disorders through alloimmune responses.

Recognised classes of red blood cell and platelet alloantigens have been described, over the past 30 years, based on observations of antibody reactions occurring when blood recipients have been exposed to blood from donors.

A recent review of human platelet alloantigen systems is provided by Ouwehand, W., and Navarrete, C., in *Molecular Haematology*, Provan, D. and Gribben, J. eds. Blackwell (1999).

Several biallelic platelet alloantigen "systems" have been characterised. In each of these systems, there are two alloantigens, each of which is provided by one of two alleles of the gene comprising the system. Because each gene occurs twice in the normal human genome, a person can be homozygous for one or the other of the two alloantigens, or heterozygous for the two alloantigens, comprising a biallelic system. The alloantigens described to date occur on glycoprotein molecules which may exist in various forms (transmembrane, GPI-linked and soluble, for example). In such a case, the alloantigens are found on each of the variant forms of the glycoprotein. For all of the biallelic platelet alloantigen systems that have been characterised at the level of protein and gene sequences, it has been found in all cases, except for one, that the difference between the two alleles is based on a single nucleotide polymorphism in the relevant gene.

One biallelic system of human platelet alloantigens is the $Gov^a/Gov^b$ biallelic system associated with CD109, a membrane glycoprotein which occurs on platelets and various other cell types, including leukocytes and endothelial cells. Each Gov allele corresponds to one CD109 glycoprotein (Sutherland, D. R. et al, 1991; Smith et al., 1995; Berry, J. et al., 2000), consistent with the known tissue distribution of CD109. The frequencies for the Gov alleles are 0.4 for $Gov^a$ and 0.6 for $Gov^b$ in the Caucasian population. Thus, in this population, 40.7% are heterozygous for the Gov alleles, and will not mount an alloimmune response due to Gov incompatibility (not possessing the Gov alloantigen found on platelets received from another). In contrast, 19.8% of Caucasians are homozygous for the $Gov^a$ allele and thus may mount an immune response due to Gov alloantigen incompatibility against platelets received from anyone in the 80.5% of the Caucasian population that is not homozygous for the $Gov^a$ allele, while 39.8% are homozygous for the $Gov^b$ allele and thus may mount an immune response due to Gov alloantigen incompatibility against platelets received from anyone in the 60.2% of the Caucasian population that is not homozygous for the $Gov^b$ allele.

As indicated above, alloimmunization based on Gov incompatibility (the introduction into the blood stream of donor platelets bearing a Gov alloantigen not carried by the recipient) can result in bleeding disorders due to platelet destruction, including NATP, PTPR, and PTP. The location of the Gov antigens within the CD109 molecule, and the nature of the CD109 polymorphism which underlies the $Gov^a/Gov^b$ alloantigen (both at the protein and at the gene level), have not heretofore been known.

Furthermore, it has not heretofore been possible to generate non-human antibody (polyclonal or monoclonal), as from a rat, mouse, goat, chicken, or the like, with specificity for the Gov$^a$ alloantigen but not the Gov$^b$ alloantigen (or vice-versa) sufficient for use in an immunoassay, for typing for Gov phenotype using platelets or CD109 molecules.

Previously developed technology, involving gene-specific amplification of platelet RNA-derived cDNA, followed by the determination of the nucleotide sequence of the amplified DNA, has been applied successfully to the elucidation of the molecular basis of other biallelic platelet alloantigen systems (Newman et al., J. Clin. Invest. 82,739-744 (1988); Newman et al., J. Clin. Invest. 83, 1778-1781 (1989)(P1A or HPA-1 system); Lyman et al., Blood 75, 2343-2348 (1990)(Bak or HPA-3system); Kuijpers et al., J. Clin. Invest. 89, 381-384 (1992)(HPA-2 or Ko system); Wang et al., J. Clin. Invest. 90, 2038-2043 (1992)(Pen system). With one exception, it has been found in each case that a single amino acid difference at a single position differentiates the amino acid sequences of the two alleles, and that this difference arises from a single allele-specific nucleotide substitution in the coding region of the mRNA and gene. There remains a need to elucidate the molecular basis of the biallelic Gov platelet alloantigen system.

SUMMARY OF THE INVENTION

The Gov a/Gov b CD109 Single Nucleotide Polymorphism

We have now discovered that a single amino acid difference in the CD109 glycoprotein distinguishes the Gov$^a$ and Gov$^b$ allelic forms. The two alleles differ at amino acid position 703 of the full-length 1445 amino acid CD109 molecule, with the Gov$^a$ allele [SEQ ID NO:2] containing a Tyr at this position, while the Gov$^b$ allele [SEQ ID NO:4] contains Ser.

Further, we have discovered that this difference in amino acid sequence between the allelic forms of CD109 is due to a single nucleotide polymorphism at position 2108 of the coding portion of full-length mRNA encoding CD109, or of the corresponding coding strand of the cDNA corresponding to this mRNA. Specifically, the Gov$^a$ allele [SEQ ID NO:1] contains adenine at position 2108, the second nucleotide of the codon encoding the amino acid at position 703 of the full-length CD109 protein, while the Gov$^b$ allele contains cytosine at position 2108, as shown in SEQ ID NO:3

The Gov$^a$/Gov$^b$ single nucleotide polymorphism of CD109, lies at position 2108 in SEQ ID NO:1. SEQ ID NO:1 is the cDNA sequence encoding the full-length 1445 amino acid CD109 precursor encoding the Gov$^a$ alleleIn the Gov$^b$ allele form [SEQ ID NO:3], C occurs at position 2108, rather than A. The ATG at the 5'-end of the sequence in SEQ ID NO:1 corresponds to the translation start of the full-length precursor form (including leader peptide) of CD109. The triplet corresponding to the N-terminal amino acid of the mature CD109 protein is at positions 64-66 in SEQ ID NO:1.

The Gov$^a$/Gov$^b$ single nucleotide polymorphism of CD109, lies at position 954 in SEQ ID NO:5. SEQ ID NO:5 is the genomic DNA sequence of human CD109 exon 19 and the contiguous introns, introns 18 and 19. The Gov$^a$/Gov$^b$ single nucleotide polymorphism of CD109 is found within CD109 exon 19, and specifically is located at position 3 of CD109 exon 19. The sequence presented in SEQ ID NO:5 contains A at position 954, and thus corresponds to the Gov$^a$ allele. The corresponding Gov$^b$ sequence contains C at position 954 of SEQ ID NO:5 (nucleotide position 3 of exon 19).

In view of this discovery, it will be readily apparent to the skilled what the present invention provides:

Gov allele-specific oligonucleotides and polynucleotides: Based on the discovery, the present invention provides oligonucleotides and polynucleotides (seems repetitive), including (but not limited to) probes which can be used to determine whether a person is homozygous for one or the other of the Gov alleles, or heterozygous for these alleles, thereby to determine that person's Gov genotype, and by extension, their Gov phenotype (i.e., the Gov alloantigen(s) which their cells express). Further, the invention provides methods of using such oligonucleotides, and test kits to facilitate their use, in such Gov genotype and phenotype determinations. These oligonucleotides of the invention can be used to determine whether, in the CD109 gene, or in the mRNA encoding CD109, the internal nucleotide (nucleotide 2108) of the codon (in CD109 gene or in the mRNA encoding CD109) which corresponds to the amino acid at position 703 in the sequence of full-length CD109 is adenine or cytosine. Such probes will typically be cDNA but may be genomic DNA, mRNA or RNA, and may be labelled for detection. The oligonucleotides of the invention can be used as probes to detect nucleic acid molecules according to techniques known in the art (for example, see U.S. Pat. Nos. 5,792,851 and 5,851,788).

For example, an oligonucleotide of the invention may be converted to a probe by being end-labelled using digoxigenin-11-deoxyuridine triphosphate. Such probes may be detected immunologically using alkaline-phosphate-conjugated polyclonal sheep antidigoxigenin F(ab) fragments and nitro blue tetrazolium with 5-bromo-4-chloro-3-indoyl phosphate as chromogenic substrate.

Gov allele-specific antibodies: Still further, based on the discovery, which underlies the invention, of the molecular basis for the Gov$^a$/Gov$^b$ alloantigen system, the invention provides non-human polyclonal and monoclonal antibodies, which can be used to distinguish one Gov allelic form of CD109 from the other, whether the CD109 is part of a complex embedded in or isolated from a membrane or is isolated. These antibodies of the invention, which are preferably provided in an aqueous buffer solution, and the immunoassays of the invention which employ such antibodies, are useful for determining whether a person has one or both of the Gov alloantigens and for Gov phenotyping. Methods of using the antibodies of the invention in the immunoassays of the invention, and in such determinations, are also encompassed by the invention. The invention also provides test kits to facilitate carrying out such immunoassays and determinations.

Gov allele-specific peptides and polypeptides: Again, based on the discovery that underlies the invention, of the molecular basis for the Gov$^a$/Gov$^b$ alloantigen system, the invention provides peptides or polypeptides, which are useful for various purposes. These peptides or polypeptides are typically between 4 and 100, and more typically between 7 and 50, amino acids in length, and have amino acid sequences identical or having sequence identity to those of segments of the CD109 sequences, that include the amino acid at position 703 of full-length mature CD109. This amino acid (position 703) corresponds the triplet at positions 2107-2109 in the CD109 cDNA sequence presented in SEQ ID NO:1, or in the corresponding sequence for the CD109 cDNA that encodes the Gov$^b$ allelic form [SEQ ID NO:3]. These peptides or polypeptides may be synthetic, may be purified from native CD109 or may be prepared by recombinant means. For guidance, one may consult the following U.S. Pat. Nos. 5,840,537, 5,850,025, 5,858,719, 5,710,018, 5,792,851, 5,851,788, 5,759,788, 5,840,530, 5,789,202, 5,871,983, 5,821,096, 5,876,991, 5,422,108, 5,612,191, 5,804,693, 5,847,258, 5,880,328, 5,767,369, 5,756,684, 5,750,652, 5,824,864, 5,763,211, 5,767,375, 5,750,848, 5,859,337, 5,563,246, 5,346,815, and WO9713843. Many of these patents also provide guidance with respect to experimental assays, probes and antibodies, methods, transformation of host cells, which are described below. These patents, like all other patents, publications (such as articles and database publications) in this application, are incorporated by reference in their entirety.

Gov allele-specific peptides and polypeptides as antigens and immunogens, and Gov allele-specific polyclonal and monoclonal antibodies: These peptides or polypeptides are useful as antigens (usually coupled to a larger, immunogenic carrier [proteinaceous or otherwise], as known in the art) for making the polyclonal or monoclonal antibodies of the invention. The peptides or polypeptides are also useful in screening monoclonal antibody-producing cultures (hybridoma cultures/*E. coli* cultures or so-called V gene phage antibodies) to identify those that produce monoclonal antibodies of the invention.

The invention also encompasses immunogenic compositions which comprise a peptide, polypeptide or fusion compound of the invention and which are immunogenic in a bird, including, without limitation, a chicken, or a mammal, such as, a mouse, rat, goat, rabbit, guinea pig, sheep or human. The compositions may include an immunogenicity-imparting "carrier" which may be but is not necessarily a protein as known in the art, that is immunogenic in a bird or mammal, coupled to at least one peptide or polypeptide of the invention, which has an amino acid sequence that is the same as that of a segment of the sequence for CD109, that includes the amino acid at position 703 of the full length CD109 molecule.

The present invention also provides methods of using the peptides, polypeptides and immunogenic compositions of the invention for making antibodies of the invention, and methods of using the peptides and polypeptides of the invention in screening monoclonal antibody-producing hybridoma cultures or bacterial clones for those that produce monoclonal antibodies or fragments thereof of the invention.

Therapeutic and diagnostic application of Gov allele-specific peptides, polypeptides, and antibodies: These peptides or polypeptides, as well as antibodies, which are specific for the $Gov^a$ [SEQ ID NO:2] or $Gov^b$ [SEQ ID NO:4], but not both, allelic forms of CD109 in the platelet membrane, and which can be produced by a mammal (including an human) immunized with the peptides or polypeptides, which themselves happen to be immunogenic, or the immunogenic compositions of the invention, are also useful both therapeutically and diagnostically. The invention also provides the methods of using the peptides and polypeptides of the invention, and antibodies made using the peptides that are immunogenic and the immunogenic compositions of the invention, in therapeutic and diagnostic applications.

The Gov allele-specific peptides or polypeptides can also be used diagnostically to detect the presence of $Gov^a$ or $Gov^b$ specific antibodies in human plasma or serum samples, using methods that are readily apparent to those skilled in the art. Such analyses would be useful in the investigation of cases of acquired alloimmune thrombocytopenia, including PTP, PTPR, and NATP. In the latter case, this approach could also be used to detect the presence of Gov allele-specific antibodies in the mother of the affected fetus or newborn. The presence of Gov allele-specific antibodies can also be detected using platelets of known Gov phenotype. However, this approach has numerous technical disadvantages that are eliminated by the use of Gov allele-specific peptides or polypeptides for Gov allele-specific antibody detection.

Administration to a person, who is suffering from, or at risk for, for example, PTP or PTPR, or a mother at risk for passing NATP-causing alloantibodies to her fetus, of one of the peptides or polypeptides, that would be bound by the anti-Gov alloantibodies in such a person, would inhibit the binding of the alloantibodies to the person's (or the fetus's platelets and thereby inhibit the platelet destruction and abnormal bleeding associated with the disorders. Alternatively, administration to such a person of antibodies (particularly human antibodies), which are produced using a peptide or polypeptide of the invention, which is immunogenic by itself, or an immunogenic composition of the invention, and which are specific for the Gov allelic form of the CD109 on the person's platelets which is associated with the PTP or PTPR, from which the person is suffering or may suffer, would induce the production of anti-idiotypic antibodies, which, in turn, would inhibit the platelet-destructive effects of the anti-Gov alloantibodies, which are generated by the person's own immune system and which are causing or threatening to cause the PTP, PTPR or NATP. These therapeutic applications of peptides and polypeptides of the invention would be especially useful in treating NATP in a newborn, because the alloantibody giving rise to NATP in the newborn is not continuously produced by the immune system of the newborn, but rather is acquired passively, and therefore in limited, non-replenished quantity, by the newborn from its mother.

Thus, in accordance with one aspect of the present invention, an oligonucleotide probe is provided that hybridizes to a portion of the CD109 gene, or a portion of CD109-encoding mRNA or cDNA prepared from such mRNA, which portion includes a nucleotide corresponding to the internal nucleotide of the codon for the amino acid at position 703 of the full-length CD109 molecule, and that is capable of distinguishing one Gov allele from the other through the ability to hybridize under stringent conditions to the portion in question only when the nucleotide in question is A (or dA), when the probe is to detect the $Gov^a$ allele, or C (or dC), when the probe is to detect the $Gov^b$ allele. The nucleotide in question is at position 2108 of the coding region of the CD109 cDNA sequence and lies at position 2108 in SEQ ID NO:1. The cDNA sequence has A at this position, and so is the sequence corresponding to the $Gov^a$ allele. The nucleotide in question lies at position 954 of the sequence presented as SEQ ID NO:5 and contains an A in this position, and thus also corresponds to $Gov^a$ allele.

The Gov allele-specific oligonucleotide hybridization probes of the invention may comprise genomic DNA, cDNA, or RNA, although preferably it is DNA. Such oligonucleotide probes can be synthesised by automated synthesis and will preferably contain about 10-30 bases, although as understood in the oligonucleotide probe hybridization assay art, as few as 8 and as many as about 50 nucleotides may be useful, depending on the position within the probe where the potential mismatch with the target is located, the extent to which a label on the probe might interfere with hybridization, and the physical conditions (e.g., temperature, pH, ionic strength) under which the hybridization of probe with target is carried out.

In accordance with another aspect of the present invention, a test kit for Gov alloantigen typing is provided comprising:
(a) means for amplifying nucleic acid that comprises at least a portion of a CD109 gene, a CD109-encoding mRNA, or a CD109 cDNA made from such RNA, wherein the portion includes a nucleotide (nucleotide 2108 in SEQ ID NO:1, or nucleotide 954 in SEQ ID NO:5) corresponding to the internal nucleotide of the codon encoding amino acid 703 of the full length CD109 protein.

(b) an oligonucleotide probe of the invention, that distinguishes one Gov allele from the other. The "means for amplifying" will, as the skilled will readily understand, depend on the amplification method to be used. Thus, for example, these means might include suitable primers, a suitable DNA polymerase, and the four 2'-deoxyribonucleoside triphosphates (dA, dC, dG, dT), if amplification is to be by the PCR method. To cite another example, if the amplification is to be by a method relying on transcription, such as the 3SR method, the means will include two primers, at least one of which, when made double-stranded, will provide a promoter, an RNA polymerase capable of transcribing from that promoter, a reverse transcriptase to function in primer-initiated, DNA-directed and RNA-directed, DNA polymerization and possibly also in RNAse H degradation of RNA to free DNA strands from RNA/RNA hybrids, the four ribonucleoside triphosphates (A, C, G and U), and the four 2'-deoxyribonucleoside triphosphates. In another example, if the amplification is by the ligase chain reaction, the means will include two oligonucleotides (DNAs) and a suitable DNA ligase that will join the two if a target, to which both can hybridize adjacent to one another in ligatable orientation, is present.

The oligonucleotide probes of the invention will preferably be labelled. The label may be any of the various labels available in the art for such probes, including, but not limited to $^{32}P$; $^{35}S$; biotin (to which a signal generating moiety, bound to or complexed with avidin can be complexed); a fluorescent moiety; an enzyme such as alkaline phosphatase (which is capable of catalysing a chromogenic reaction); digoxigenin, as described above; or the like.

As indicated in the examples, RFLP analysis can be employed, using BstNI (or isoschizomers thereof), in analysing cDNA or genomic DNA (with or without amplification) to determine Gov genotype. As indicated further in the examples, electrophoretic SSCP analysis may be used to determine Gov genotype. And as indicated in the examples, the hybridization studies outlined above may use fluorescent probes, and may be directly coupled to the DNA amplification step, as in "Real-Time PCR" or related methods.

There has also been provided, in accordance with another aspect of the present invention, a method of typing for Gov allele-specific target sequence in a CD 109 nucleic acid derived from a subject, comprising the steps of,
(a) obtaining, by a target nucleic acid amplification process applied to mRNA from human platelets, endothelial cells, or T cells, an assayable quantity of amplified nucleic acid with a sequence that is that of a subsequence (or the complement of a subsequence) of the mRNA that encodes a CD109 said subsequence including the nucleotide at the position in the mRNA corresponding to position 2108 in SEQ ID NO:1 or to nucleotide 954 in SEQ ID NO:5; and
(b) analyzing (e.g., in a nucleic acid probe hybridization assay employing an oligonucleotide probe or probes according to the invention) the amplified nucleic acid obtained in step (a) to determine the base or bases at the position in the amplified nucleic acid that corresponds to position 2108 in SEQ ID NO:1 or to nucleotide 954 in SEQ ID NO:5. It is noteworthy that, if the product of the amplification is double-stranded DNA, analysis for Gov genotype can be carried out by a RFLP (restriction fragment length polymorphism) analysis comprising exposing the amplified DNA to the restriction endonuclease BstNI (or isoschizomer thereof) under conditions whereby the DNA will be cleaved if it includes a site for cleavage by that enzyme. Such DNA, prepared from mRNA encoding the $Gov^b$ alloantigen, containing a C rather than an A at the position corresponding to nucleotide 2108 in SEQ ID NO:1 (or to nucleotide 954 in SEQ ID NO:5), includes a recognition site for that endonuclease, while such DNA prepared from mRNA encoding the $Gov^a$ alloantigen, does not If the analysis, by whatever method, of the amplified nucleic acid reveals that there is only an A (or dA) at the position corresponding to position 12108, the platelets (and blood from which they came) have only the $Gov^a$ alloantigen, and the individual from whom the platelets came, is homozygous for $Gov^a$. Alternatively, if the analysis of the amplified nucleic acid reveals that there is only a C (or dC) at the position corresponding to position 2108, the platelets (and blood from which they came) have only the $Gov^b$ alloantigen and the individual, from whom the platelets came, is homozygous for the $Gov^b$ allele. Finally, if the analysis indicates that there is either an A (or dA) or a C (or dC) at that position, the platelets (and blood from which they came) have both Gov alloantigens, and the individual from whom the platelets came, is heterozygous for Gov alloantigen.

In one application of the typing methods of the invention, the methods are applied to two individuals to determine whether blood or platelets from one would provoke an alloimmune response, and possibly PTP or PTPR, in the other. The typing method can be applied with a man and a woman, who are contemplating conceiving or have conceived a child together, to determine the risk that the child would be at risk for NATP and the risk that the woman would be at increased risk for PTP or PTPR. If the woman were heterozygous for the Gov alloantigens there would be, due to Gov alloantigen incompatibility, no risk of NATP and no increased risk for the woman of PTP or PTPR. If, however, the woman were homozygous for one of the Gov alloantigens, there would be, due to Gov alloantigen incompatibility, risk of NATP in a child and increased risk of PTP or PTPR for the woman, unless the man is homozygous for the same Gov alloantigen as is the woman.

In accordance with yet another aspect of the present invention, a method of typing an individual for Gov alloantigen is provided that comprises analyzing the genomic DNA of the individual to determine the Gov alloantigen(s) of the individual. Applications of this method are substantially the same as those of the method of the invention for typing for Gov alloantigen that begins with platelet, endothelial cell, or T cell mRNA.

This method of the invention, entailing analysis of genomic DNA, can be carried out in substantially the same way as outlined above for analysis of mRNA, namely first amplifying the genomic DNA and then analyzing to product of the amplification to ascertain whether there is only dA, only dC, or both dA and dC, at the position in the coding region of the genomic DNA corresponding to position 2108 in SEQ ID NO:1, or to nucleotide 954 in SEQ ID NO:5.

In accordance with a further aspect of the present invention, a test kit for Gov alloantigen typing is provided comprising a non-human antibody (or antibodies) that distinguishes the two allelic forms of CD109. The antibody (or antibodies) of the kit may be polyclonal, or preferably monoclonal, and in addition to its (their) specificity for either but not both Gov alloantigens (on the surface of platelets or separated therefrom) or the CD109 subunit of one but not both of such alloantigens, typically will recognise a polypeptide molecule encoded by a nucleotide sequence encoding at least amino acid 703 of a CD109 polypeptide (the amino acid at the position corresponding to nucleotides 2107-2109 in SEQ ID NO:1, or to nucleotides 953-955 in SEQ ID NO:5).

The invention relates to an oligonucleotide comprising a sequence which binds specifically to (i) a region of CD109 nucleic acid that includes a single nucleotide polymorphism that is distinctive of a Gov$^a$ allele and/or (ii) a region of CD109 nucleic acid that includes a single nucleotide polymorphism that is distinctive of a Gov$^b$ allele. The oligonucleotide optionally comprises 8 to 50 nucleotides. The oligonucleotide preferably specifically binds to one of (i) or (ii) under high stringency hybridization conditions. The stringent hybridization conditions optionally comprise 0.1XSSC, 0.1% SDS at 65° C. The CD109 nucleic acid optionally comprises genomic DNA, cDNA, or RNA corresponding to the Gov$^a$ allele of the CD109 gene or locus, or comprises genomic DNA, cDNA, or RNA corresponding to the Gov$^b$ allele of the CD109 gene or locus. The Gov$^a$ allele optionally comprises an A at a position corresponding to position 2108 of SEQ ID NO:1 and corresponding to position 954 of SEQ ID NO:5. The Gov$^b$ allele optionally comprises a C at a position corresponding to position 2108 of SEQ ID NO:3 and corresponding to position 954 of SEQ ID NO:5. The oligonucleotide optionally comprises a sequence complementary to the Gov$^a$ allele or to the Gov$^b$ allele. The oligonucleotide optionally comprises a sequence selected from the group consisting of:
(a) 8-50 nucleotides of SEQ ID NO:1;
(b) a sequence that is complementary to a sequence specified in (a); and
(c) a sequence having at least 70% sequence identity to a sequence in (a) or (b), wherein the sequence having identity is capable of hybridization to C109 under high stringency hybridization conditions.

The oligonucleotide optionally comprises a sequence selected from the group consisting of:
(a) 8-50 nucleotides of SEQ ID NO:3;
(b) a sequence that is complementary to a sequence specified in (a); and
(c) a sequence having at least 70% sequence identity to a sequence in (a) or (b), wherein the sequence having identity is capable of hybridization to CD109 under high stringency hybridization conditions.

The oligonucleotide optionally comprises all or part of any one of SEQ ID NO:6-SEQ ID NO:14 or a complement thereof. The oligonucleotide optionally comprises 8 to 50 nucleic acids. The nucleic acid is capable of use as a probe in a hybridization assay. The nucleic acid sequence is typically detectably labelled. The detectable label optionally comprises:
(a) a fluorogenic dye; and/or
(b) a biotinylation modification; and/or
(c) a radiolabel.

The oligonucleotide sequence optionally comprises DNA, a DNA analog, RNA or an RNA analog. The oligonucleotide is optionally attached to a substrate. The oligonucleotide is optionally capable of use as a primer that will specifically bind proximate to, and/or cause elongation through, a CD109 sequence, including the single nucleotide polymorphism distinctive of the Gov$^a$ or Gov$^b$ alleles.

Another aspect of the invention relates to a Gov genotyping kit comprising a detection agent for detecting the presence of a Gov allele-specific target sequence in a CD109 nucleic acid derived from a subject. The detection agent optionally comprises comprises a nucleic acid and/or a restriction enzyme. The kit optionally further comprises a container. The container optionally comprises a biological sample container for housing the detection agent. The kit optionally further comprises a plate having a plurality of wells and having bound thereto probes having a nucleic acid sequence which specifically binds to a C109 sequence including a Gov$^a$ or a Gov$^b$ allele target sequence. The restriction enzyme is optionally selected from the group consisting of Bst2UI, BstNI, BstOI, EcoRII, MaeIII, MspR91, MvaI, ScrFI or an isoschizomer thereof. The kit optionally further comprises an amplification agent for amplifying the nucleic acid. The amplification agent amplifies a region of CD109 platelet, T cell, or endothelial cell mRNA including the single nucleotide polymorphism distinctive of a Gov$^a$ or Gov$^b$ allele. The amplification agent optionally comprises a primer set including first and second primers, wherein the first primer is a nucleic acid that will specifically bind proximate to, and/or cause elongation through, CD109 sequence that includes the single nucleotide polymorphism distinctive of a Gov$^a$ allele and the second primer is a nucleic acid that will specifically bind proximate to, and/or cause elongation through, CD109 sequence that includes the single nucleotide polymorphism distinctive of a Gov$^b$ allele. The nucleic acid is optionally obtained by amplification with all or part of the nucleic acid of any one of SEQ ID NO:6-SEQ ID NO:14 or he complement thereof. The kit optionally further comprises all or part of a CD109 gene, a CD109-encoding mRNA, or a CD109 cDNA made from a CD109-encoding mRNA. The kit optionally further comprises the oligonucleotide of the invention. The kit is useful for detecting that the subject has or is at risk of a disease, disorder or abnormal physical state, such as a blood disease, disorder or abnormal physical state which in some cases may comprise bleeding of the subject, or increased risk of bleeding, due to destruction of blood platelets. The blood disease, disorder or abnormal physical state will often be post-transfusion purpura ("PTP"), post-transfusion platelet refractoriness ("PR") or neonatal alloimmune thrombocytopenia ("NAIT"). The nucleic acid for the kit and methods is usually obtained from mRNA from human platelets, T cells, endothelial cells, or human genomic DNA.

Another aspect of the invention relates to a method of Gov alloantigen genotyping a subject comprising:
(a) providing a CD109 nucleic acid sample derived from the subject; and
(b) detecting a region of CD109 nucleic acid that includes a single nucleotide polymorphism distinctive of a Gov$^a$ or a Gov$^a$ allele.

The method preferably comprises determining whether the subject is homozygous or heterozygous for the Gov alleles. The subject of the methods will typically be a human and the Gov genotype is used to determine that the subject has, or is at risk of a disease, disorder or abnormal physical state, such as a blood disease, disorder or abnormal physical state for example, comprising bleeding of the subject, or increased risk of bleeding, due to destruction of blood platelets. Examples of blood disease, disorder or abnormal physical state include post-transfusion purpura ("PTP"), post-transfusion platelet refractoriness ("PR") or neonatal alloimmune thrombocytopenia ("NAIT"). The nucleic acid is typically obtained by amplifying the nucleic acid from the subject. The nucleic acid is preferably obtained by amplification with all or part of an oligonucleotide of the invention. The nucleic acid is typically obtained from mRNA from human platelets, T cells, endothelial cells, or human genomic DNA. The detection step optionally comprises determining the nucleotide sequence of the CD109 nucleic acid or contacting the nucleic acid with the oligonucleotide under high stringency conditions. In a hybridization step, the oligonucleotide will optionally selectively hybridize to (i) a region of CD109 nucleic acid that includes a single polymorphism distinctive of a Gov$^a$ allele or (ii) a region of CD109 nucleic acid that includes a single polymorphism distinctive of a Gov$^b$ allele. The detecting step optionally comprises:
(a) performing a restriction endonuclease digestion of the nucleic acid, thereby providing a nucleic acid digest; and
(b) contacting the digest with the oligonucleotide.

Hybridization optionally occurs either during or subsequent to PCR amplification and the analysis is optionally by "Real-Time" PCR analysis, or fluorimetric analysis. The detection step optionally comprises:
(a) incubation of the amplified nucleic acid with a restriction endonuclease under conditions whereby the DNA will be cleaved if the nucleic acid comprises a recognition site for the enzyme; and
(b) determining whether the nucleic acid contains a recognition site for the restriction enzyme characteristic of cDNA made from mRNA encoding a Gov$^a$ or Gov$^b$ allele of CD109.

The restriction enzyme is, for example, selected from the group consisting of Bst2UI, BstNI, BstOI, EcoRII, MaeIII, MspR91, MvaI, ScrFI or an isoschizomer thereof. The determination step optionally includes size analysis of the nucleic acid. The amplified nucleic acid is optionally analyzed by electrophoretic mobility and the mobility of the amplified nucleic acid is compared to the characteristic mobility of amplified nucleic acid fragments corresponding to the Gov$^a$ or Gov$^b$ alleles of CD109. The method of amplifying CD109 mRNA optionally comprises amplifying the mRNA by PCR using an oligonucleotide of the invention. Another aspect of the invention relates to a Gov$^a$ specific antibody. The antibody that recognizes specifically a Gov$^a$ allele-specific CD109 epitope corresponding to the polypeptide encoded by a CD109 nucleic acid optionally contains an A at the position corresponding to position 2108 of SEQ ID NO:1 and position 954 of SEQ ID NO:5., and containing the amino acid Tyrosine at the position corresponding to position 703 of the CD109 protein encoded by SEQ ID NO:1. Another aspect of the invention relates to a Gov$^b$ specific antibody. The antibody that recognizes specifically a Gov$^b$ allele-specific CD109 epitope corresponding to the polypeptide encoded by a CD109 nucleic acid optionally contains a C at the position corresponding to position 2108 of SEQ ID NO:3 and position 954 of SEQ ID NO:5., and containing the amino acid Serine at the position corresponding to position 703 of the CD109 protein encoded by SEQ ID NO:3. The antibody is typically a monoclonal antibody or a polyclonal antibody and further comprises a detectable label. Another aspect of the invention relates to an immunogenic composition comprising a Gov specific antibody. The method of Gov alloantigen phenotyping a subject, optionally comprises:
(a) providing a CD109 polypeptide sample derived from the subject; and
(b) detecting the presence of a Gov$^a$ or a Gov$^b$ antigen in the CD109 polypeptide.

The CD109 is typically membrane bound CD109 or isolated CD109. The detection step optionally comprises contacting the polypeptide sample with an antibody described herein. A diagnostic kit for Gov alloantigen phenotyping a subject, optionally comprises a Gov$^a$ antibody and/or a Gov$^b$ antibody of the invention. The kit optionally further comprises a container.

The invention also includes an isolated polypeptide containing a Gov$^a$ allele-specific amino acid sequence and which is specifically reactive with a Gov$^a$ antibody. The invention also includes an isolated polypeptide containing Gov$^a$ allele-specific amino acid sequence and which is specifically reactive with a Gov$^b$ antibody. The isolated polypeptide optionally comprises between 4 and 100 amino acids. The isolated polypeptide also optionally comprises a full-length CD109 polypeptide, or a fragment of a CD109 polypeptide. The invention also includes an isolated CD109 polypeptide fragment, comprising a Gov$^a$ or a Gov$^b$ antigen.

The polypeptide fragment optionally comprises all of, or a fragment of, the protein encoded by SEQ ID NO:1., and in which the amino acid corresponding to position 703 of the protein encoded by SEQ ID NO:1 is a Tyrosine. The polypeptide fragment optionally comprises all of, or a fragment of, the protein encoded by SEQ ID NO:3., and in which the amino acid corresponding to position 703 of the protein encoded by SEQ ID NO:3 is a Serine. The polypeptide fragment optionally comprises between 4 and 100 amino acids. The polypeptide fragment of optionally comprises between 7 and 50 amino acids. The polypeptide is optionally purified from native CD109, or is synthetic, or is prepared by recombinant means. The polypeptide fragment is optionally bound to a substrate. The invention also includes a fusion compound comprising the polypeptide of the invention-connected to an immunogenic carrier. The fusion compound typically includes an immunogenic carrier comprising a proteinaceous carrier. The immunogenic carrier optionally comprises a detectable label. The invention also includes a Gov$^a$ or Gov$^b$ specific antibody recognizing the fusion compound. The invention also includes an immunogenic composition comprising the polypeptide, polypeptide fragment or fusion compound. Another aspect of the invention relates to a method of producing a Gov$^a$ or Gov$^b$ specific antibody, comprising contacting an animal with the immunogenic composition so that the animal produces antibodies against the immunogenic composition. The animal is typically a bird or a mammal.

The invention also includes a method of screening an antibody producing culture to determine whether the culture produces Gov$^a$ or Gov$^b$ specific antibody, comprising:
(a) contacting a polypeptide of the invention with the culture; and
(b) detecting Gov$^a$ or Gov$^b$ specific antibody.

The polypeptide typically comprises a detectable label. The polypeptide is optionally attached to a substrate. The invention also includes a method of purifying a Gov allele-specific antibody from a sample, comprising:
(a) contacting a Gov allele-specific antibody with a polypeptide of the invention comprising a Gov$^a$ or Gov$^b$ antigen, so that an antibody:polypeptide complex is formed;
(b) separating the complex from the sample; and
(c) next separating the antibody from the polypeptide.

The polypeptide is optionally bound to a substrate. The polypeptide optionally comprises a detectable label. Another aspect of the invention relates to a method of purifying a Gov polypeptide from a sample, comprising:
(a) contacting a Gov allele-specific antibody with a polypeptide of the invention containing a Gov$^a$ or Gov$^b$-specific epitope, so that an antibody: polypeptide complex is formed;
(b) separating the complex from the sample; and
(c) next separating the antibody from the polypeptide.

The antibody is optionally bound to a substrate. The antibody optionally comprises a detectable label.

The invention also includes a method of screening a subject sample to determine whether the sample contains Gov$^a$ or Gov$^b$-specific antibodies, comprising:
(a) contacting a polypeptide of the invention with the sample; and
(b) detecting the presence or absence of Gov$^a$ or Gov$^b$ specific antibody.

The polypeptide optionally comprises a detectable label. The polypeptide is optionally attached to a substrate The subject optionally comprises a mother of a fetus or a newborn infant, or the fetus or newborn infant itself, and the presence of $Gov^a$ or $Gov^b$-specific antibody indicates that the fetus or infant has, or is at risk of NAIT. in such a case, the presence of $Gov^a$ or $Gov^b$ specific antibody indicates that the subject has, or is at risk of a blood disease, disorder or abnormal physical state, for example, that comprises bleeding of the subject, or increased risk of bleeding, due to destruction of blood platelets. The blood disease, disorder or abnormal physical state typically comprises post-transfusion purpura ("PTP"), post-transfusion platelet refractoriness ("PR") or neonatal alloimmune thrombocytopenia (NAIT). The sample optionally comprises human serum or plasma. Another aspect of the invention relates to a diagnostic kit for detection of $Gov^a$ or $Gov^b$ specific antibody, comprising a polypeptide described herein. The kit optionally further comprises a container.

Another aspect of the invention relates to a method of determining Gov antibody specificity, comprising:

(a) contacting an antibody with a first polypeptide comprising a $Gov^a$ antigen and a second polypeptide comprising a $Gov^b$ antigen; and (b) determining whether the antibody binds to either or both of the first and second polypeptide.

Another aspect involves a method of blocking $Gov^a$ antibody binding to an antigen, comprising: contacting the antibody with a polypeptide of the invention comprising a $Gov^a$ antigen so that an antibody: polypeptide complex is formed. In the method, the polypeptide optionally comprises a detectable label. The polypeptide is optionally bound to a substrate. The invention also includes a pharmaceutical composition comprising the polypeptide. The invention also relates to a method of blocking $Gov^b$ antibody binding to an antigen, comprising: contacting the antibody with a polypeptide of the invention comprising a $Gov^b$ antigen so that an antibody: polypeptide complex is formed. The polypeptide optionally comprises a detectable label. The polypeptide is optionally bound to a substrate. The invention also includes a pharmaceutical composition comprising the polypeptide. Another aspect of the invention relates to a method of immunizing a subject so that the subject will produce anti-idiotypic antibodies, comprising administering to the subject the immunogenic composition.

The invention also includes a method of blocking $Gov^a$ or $Gov^b$ specific antibodies from binding to CD109 in a subject, comprising: administering to the subject polypeptides of the invention capable of binding to $Gov^a$ and/or $Gov^b$ specific antibodies. The subject has or is at risk of a blood disease, disorder or abnormal physical state. The polypeptide optionally comprises a detectable label. The binding of the polypeptide to the $Gov^a$ or $Gov^b$ specific antibody prevents alloimmune cell destruction by the antibody. The binding of the polypeptide to the $Gov^a$ or $Gov^b$ -specific antibody depletes the antibody. The blood disease, disorder or abnormal physical state typically comprises bleeding of the subject, or increased risk of bleeding, due to alloimmune destruction of blood platelets, such as post-transfusion purpura ("PTP"), post-transfusion platelet refractoriness ("PR") or neonatal alloimmune thrombocytopenia ("NAIT").

DETAILED DESCRIPTION OF THE INVENTION

Definitions

The following definitions are provided in order to aid those skilled in the art in understanding the detailed description of the present invention.

The term "alloantigens" refers to antigens of an individual that are responsible for eliciting an alloimmune response.

The phrase "alloimmune response" refers to an immune response, which occurs when antibodies from one individual react against antigens of a different individual of the same species.

The phrase "anti-idiotypic antibodies" refers to antibodies which can bind endogenous or foreign idiotypic antibodies and which can be used to treat or prevent pathological conditions associated with an immune response to a foreign alloantigen.

The phrase "$Gov^a/Gov^b$ biallelic system" refers to a system of human platelet alloantigens in which an individual can be homozygous for either $Gov^a$ or $Gov^b$ allelic forms of CD 109, or an individual can be $Gov^a/Gov^b$ heterozygous for CD109.

"GPI" refers to glycosylphosphatidylinositol.

The term "NATP" refers to neonatal alloimmune thrombocytopenia.

"Nucleic acid" includes DNA and RNA, whether single or double stranded. The term is also intended to include a strand that is a mixture of nucleic acids and nucleic acid analogs and/or nucleotide analogs, or that is made entirely of nucleic acid analogs and/or nucleotide analogs.

"Nucleic acid analogue" refers to modified nucleic acids or species unrelated to nucleic acids that are capable of providing selective binding to nucleic acids or other nucleic acid analogues. As used herein, the term "nucleotide analogues" includes nucleic acids where the internucleotide phosphodiester bond of DNA or RNA is modified to enhance biostability of the oligomer and "tune" the selectivity/specificity for target molecules (Ulhmann, et al., 1990, Angew. Chem. Int. Ed. Eng., 90: 543; Goodchild, 1990, J. Bioconjugate Chem., I: 165; Englisch et al., 1991, Angew, Chem. Int. Ed. Eng., 30: 613). Such modifications may include and are not limited to phosphorothioates, phosphorodithioates, phosphotriesters, phosphoramidates or methylphosphonates. The 2'-O-methyl, allyl and 2'-deoxy-2'-fluoro RNA analogs, when incorporated into an oligomer show increased biostability and stabilization of the RNA/DNA duplex (Lesnik et al., 1993, Biochemistry, 32: 7832). As used herein, the term "nucleic acid analogues" also include alpha anomers (α-DNA), L-DNA (mirror image DNA), 2'-5' linked RNA, branched DNA/RNA or chimeras of natural DNA or RNA and the above-modified nucleic acids. For the purposes of the present invention, any nucleic acid containing a "nucleotide analogue" shall be considered as a nucleic acid analogue. Backbone replaced nucleic acid analogues can also be adapted to for use as immobilised selective moieties of the present invention. For purposes of the present invention, the peptide nucleic acids (PNAs) (Nielsen et al, 1993, Anti-Cancer Drug Design, 8: 53; Engels et al., 1992, Angew, Chem. Int. Ed. Eng., 31: 1008) and carbamate-bridged morpholino-type oligonucleotide analogs (Burger, D. R., 1993, J. Clinical Immunoassay, 16: 224; Uhlmann, et al., 1993, Methods in Molecular Biology, 20,. "Protocols for Oligonucleotides and Analogs," ed. Sudhir Agarwal, Humana Press, NJ, U.S.A., pp. 335-389) are also embraced by the term "nucleic acid analogues". Both exhibit sequence-specific binding to DNA with the resulting duplexes being more thermally stable than the natural DNA/DNA duplex. Other backbone-replaced nucleic acids are well known to those skilled in the art and may also be used in the present invention (See e.g., Uhlmann et al 1993, Methods in Molecular Biology, 20, "Protocols for Oligonucleotides and Analogs," ed. Sudhir Agrawal, Humana Press, NJ, U.S.A., pp. 335).

The term "PTP" refers to post-transfusion purpura.

The term "PTPR" refers to post-transfusion platelet refractorines.

"SNP" refers to single nucleotide polymorphism.

The standard, one-letter codes "A," "C," "G," and "T" are used herein for the nucleotides adenylate, cytidylate, guanylate, and thymidylate, respectively. The skilled will understand that, in DNAs, the nucleotides are 2'-deoxyribonucleotide-5'-phosphates (or, at the 5'-end, possibly triphosphates) while, in RNAs, the nucleotides are ribonucleotide-5'-phosphates (or, at the 5'-end, possibly triphosphates) and uridylate (U) occurs in place of T. "N" means any one of the four nucleotides. On occasion herein, dA, dC, dG and dT might be used for the respective 2'-deoxyribonucleotides.

Unless otherwise specified or required by the context, "nucleic acid" means DNA or RNA and "nucleotide" means ribonucleotide or 2'-deoxyribonucleotide.

Reference herein to a "full-length" CD109 molecule or protein means the 1445-amino acid-long polypeptide, for which the amino acid sequence, deduced from a cDNA sequence, is provided in SEQ ID NO:1 and in SEQ ID NO:3 and which is denoted as the full-length translated product (i.e., including the amino-terminal leader peptide, and excluding carboxyl-terminal processing associated with GPI anchor addition). The $Gov^a$ alloantigen bearing form of CD109 may be referred to herein as $^{703}$Tyr CD109. The $Gov^b$ alloantigen bearing form of CD109 may be referred to herein as $^{703}$Ser CD109.

It has been determined that a single nucleotide of the CD109 gene is responsible for the Gov polymorphism in CD109. Extensive serological studies initially demonstrated that the polymorphism underlying the Gov system resides solely on the CD109 molecule [Sutherland, D. R. (1991); Smith et al. (1995)]. Further, extensive deglycosylation of CD109 does not affect the binding the anti-$Gov^a$ and anti-$Gov^b$ antibodies to molecules of the appropriate phenotype, or to cells bearing the appropriate CD109 variant, indicating that carbohydrate residues are not involved in the formation of Gov antigenic epitopes. Further work has indicated that the Gov allele-specific antibody binding can however, be abrogated by denaturation of CD109 with the detergent SDS [Smith et al. (1995)]. Taken together, these observations indicate that the Gov alleles of CD109 are protein epitopes that are likely defined by the primary amino acid sequence of CD109.

Following the isolation of a CD109 cDNA the nature of the two Gov alleles was characterised further using platelet RNA-derived cDNA in the polymerase chain reaction ("PCR"). Platelet mRNA transcripts were obtained from serologically defined $Gov^{a/a}$, $Gov^{a/b}$ and $Gov^{b/b}$ individuals. The RNA was then converted to cDNA, and the entire CD109 cDNA coding region was then amplified as a series of overlapping PCR products. The $Gov^a$ [SEQ ID NO:1] and $Gov^b$ [SEQ ID NO:3] alleles differ by an A to C substitution at position 2108 of the coding region of the CD109 cDNA. This single nucleotide polymorphism also results in a BstNI restriction site in the $Gov^b$ allele that is not present in its $Gov^a$ counterpart. On the basis of this BstNI site, $Gov^a$ can by distinguished from $Gov^b$ by restriction fragment length polymorphism (RFLP) analysis. This single nucleotide polymorphism can also be detected by SSCP analysis, and by allele-specific hybridization studies, including "Real-Time" PCR analyses.

As a result of this $A^{2108}C$ single nucleotide polymorphism, the $Gov^a$ allele [SEQ ID NO:2] of CD109 contains a Tyr at position 703 of the full-length protein, while the $Gov^b$ allele [SEQ ID NO:4] contains a Ser in this position. The polymorphism does not alter the ability of $Gov^a$ and $Gov^b$ homozygous platelets to adhere to collagen types I, III and V. Additionally, the binding of anti-$Gov^a$ and ant-$Gov^b$ antibodies to platelets of the appropriate phenotype did not interfere with platelet adhesion to any of the above collagen types. Thus, while the Tyr$^{703}$Ser results in the formation of the Gov alloantigen epitopes, it does not appear to impair platelet function.

Identification and characterisation of the Gov alloantigen system permits pre- and post-natal diagnosis of the Gov phenotype of an individual, providing a warning for the possibility of NATP, PTP and PTPR. Allelic Gov typing of CD109 equates with the Gov status of the CD109 protein of an individual. The Gov system led to diagnostic and therapeutic strategies to avoid or control diseases that result from Gov incompatibility. The present invention can be applied to these tasks and goals in a variety of ways, illustrative examples of which are discussed below.

For example, an oligonucleotide probe can be synthesized, in accordance with the present invention, that will hybridize to a cDNA segment, derived from CD109 mRNA, that contains the nucleotide G at polymorphic nucleotide 2108 (nucleotide=guanylate). Alternatively, an oligonucleotide probe can be synthesized that will hybridize with a CD109 cDNA segment containing the base adenine at nucleotide 2108. (nucleotide=adenylate). These allele-specific probes can be appropriately labelled and added to the generated cDNA segments under annealing conditions, such that only one of the allele-specific probes hybridizes and can be detected, thereby identifying the specific $Gov^a$ or $Gov^b$ allele. In accordance with conventional procedures, the design of an oligonucleotide probe according to the present invention preferably involves adjusting probe length to accommodate hybridization conditions (temperature, ionic strength, exposure time) while assuring allele-specificity. A length of ten to thirty nucleotides is typical.

Diagnostic kits can also be used, in accordance with the present invention, for the determination and diagnosis of alloantigen phenotypes via the procedures described herein. Such a kit can include, among others, antibodies or antibody fragments to an antigenic determinant expressed by either of the above-described $Gov^a$-and $Gov^b$-encoding sequences. These antibodies would react with the blood sample of an individual so as to indicate whether that individual has a $Gov^a$ or $Gov^b$ phenotype. Alternatively, all the reagents required for the detection of nucleotide(s) that distinguish the Gov alloantigens, by means described herein, can be provided in a single kit that uses isolated genomic DNA, platelet (or other cellular) mRNA or total RNA, or corresponding cDNA from an individual. A kit containing a labelled probe that distinguishes, for example, nucleotide 2108 of CD109 can be utilised for Gov alloantigen genotyping and phenotyping.

A further beneficial use of the nucleotide sequences that distinguish the $Gov^a$ allele from the $Gov^b$ allele is to obtain or synthesize the respective expression product, in the form of a peptide or polypeptide, encoded by these nucleotide sequences. These polypeptides can be used to generate antibodies for diagnostic and therapeutic uses, for example, with regard to pathological conditions such as PTP, PTPR or NATP. These polypeptides can also be used diagnostically to detect the presence of $Gov^a$ or $Gov^b$ specific antibodies in patient plasma or serum, or used therapeutically (see below; assays may be adopted, for example, from U.S. Pat. No. 5,851,788).

A polypeptide within the present invention which can be used for the purpose of generating such antibodies preferably comprises an amino-acid sequence that corresponds to (i.e., is coincident with or functionally equivalent to) a fragment of the CD109 molecule that includes amino acid 703. When amino acid 703 is Tyrosine, the polypeptide can be used, as described above, to produce antibodies that specifically bind the $Gov^a$ form of CD109; in contrast, when it is Serine, antibodies can be obtained that specifically recognise the $Gov^b$ form. The class of polypeptides thus defined, in accordance with the present invention, is not intended to include the native CD109 molecule, but does encompass fragments of the molecule, as well as synthetic polypeptides meeting the aforementioned definition.

Although the length of a polypeptide within this class is not critical, the requirement for immunogenicity may require that the polypeptide be attached to an immunogenicity-imparting carrier. Such carriers include a particulate carrier such as a liposome or a soluble macromolecule (protein or polysaccharide) with a molecular weight in the range of about 10,000 to 1,000,000 Daltons Additionally, it may be desirable to administer the polypeptide with an adjuvant, such as complete Freund's adjuvant For artificial polypeptides, as distinguished from CD109 fragments, maximum length is determined largely by the limits of techniques available for peptide synthesis, which are currently about fifty amino acids. Thus, a synthetic polypeptide of the present invention is preferably between four to about fifty amino acids in length.

In the context of the present invention, the term "antibody" encompasses monoclonal and polyclonal antibodies produced by any available means. Such antibodies can belong to any antibody class (IgG, IgM, IgA, etc.) and may be chimeric. Examples of the preparation and uses of polyclonal antibodies are disclosed in U.S. Pat. Nos. 5,512,282, 4,828,985, 5,225,331 and 5,124,147 which are incorporated by reference in their entirety The term "antibody" also encompasses antibody fragments, such as Fab and F(ab')$_2$ fragments, of anti-Gov$^a$ or anti-Gov$^b$ antibodies, conjugates of such fragments, and so-called "antigen binding proteins" (single-chain antibodies) which are based on anti-Gov$^a$ or anti-Gov$^b$ antibodies, in accordance, for example, with U.S. Pat. No. 4,704,692, the contents of which are hereby incorporated by reference. Alternatively, monoclonal antibodies or fragments thereof within the present invention can be produced using conventional procedures via the expression of isolated DNA that encodes variable regions of such a monoclonal antibody in host cells such as *E. coli* (see, e.g., Ward et al., Nature, 341:544-546 (1989)) or transfected murine myeloma cells (see Gillies et al., Biotechnol. 7:799-804 (1989); Nakatani et al., Biotechnol. 7:805-810 (1989)). For additional examples of methods of the preparation and uses of monoclonal antibodies, see U.S. Pat. Nos. 5,688,681, 5,688,657, 5,683,693, 5,667,781, 5,665,356, 5,591,628, 5,510,241, 5,503,987, 5,501,988, 5,500,345 and 5,496,705 that are incorporated by reference in their entirety.

While human alloantisera currently used for serological typing are specifically excluded from this definition, the use of CD109 or Gov allele-specific peptides to detect anti-Gov antibodies in human plasma or serum, or to determine the specificity of such alloantibodies, are specifically included. Similarly, the use of such CD109 peptides or Gov allele-specific peptides to purify CD109 antibodies, or allele-specific CD109 antibodies from human serum is specifically included. Similarly, the use in vitro of such CD109 peptides or Gov allele-specific peptides to deplete allele-specific antibody activity from human serum samples, or to block CD109 antibody binding, or allele-specific antibody binding, is specifically included.

Diagnostic applications of these antibodies are exemplified, according to the present invention, by the use of a kit containing an anti-Gov$^a$ or an anti-Gov$^b$ antibody, which undergoes a reaction with a sample of an individual's blood to determine a Gov$^a$ or Gov$^b$ platelet phenotype. Such a reaction involves the binding of anti-Gov$^a$ antibody to Gov$^a$ antigen or the binding of anti-Gov$^b$ antibody to Gov$^b$ antigen. The observation of antibody-antigen complex in a blood sample would indicate a positive result. A kit of this type could be used to diagnose, or to help prevent the occurrence of pathological conditions like PTP, PTPR, or NATP.

A polypeptide of the present invention that is recognised specifically by anti-Gov$^a$ or ant-Gov$^b$ antibodies can also be used therapeutically. Thus, antibodies raised against such a polypeptide can be employed in the generation, via conventional methods, of anti-idiotypic antibodies, that is, antibodies that bind an anti-Gov$^a$ or anti-Gov$^b$ antibody. See, e.g., U.S. Pat. No. 4,699,880, the contents of which are hereby incorporated by reference. Such anti-idiotypic antibodies would bind endogenous or foreign anti-Gov antibodies in the blood of an individual, which would treat or prevent pathological conditions associated with an immune response to a "foreign" Gov alloantigen. Alternatively, a polypeptide within the present invention can be administered to an individual, with a physiologically-compatible carrier, to achieve the same qualitative effect, namely, the selective reduction or elimination of circulating anti-Gov antibodies from a patient suffering or at risk from an immune response, or the abrogation by competitive binding to administered peptide, of the binding of Gov-specific antibodies to the platelets of such an individual The present invention is further described below by reference to the following, illustrative examples.

EXAMPLE 1

PCR Amplification and Analysis of PCR Products

Platelet total RNA was isolated from EDTA anticoagulated blood of Gov$^{aa}$ and Gov$^{bb}$ individuals in the manner described in Lymann et al., Blood 75:2343-48 (1990). First, platelet mRNA in 10 µl aliquots was heated to 70° C. for 10 minutes and quickly cooled on ice before reverse transcription. The first strand cDNA was then synthesized using 10 µM oligo dT, 40 units RNAsin (Promega), 2 mM of each dNTP (dN triphosphate) (Pharmacia), 500 units of cloned MMLV reverse transcriptase and 5× enzyme buffer (Gibco) in a total volume of 50 µl. The cDNA synthesis was carried out at 42° C. for 45 minutes and was stopped by chilling to 0° C.

Overlapping sets of oligonucleotide primers (Table 2) based on the sequence of CD109 were then used to amplify by PCR the entire coding region of platelet CD109 in 8 overlapping segments that spanned the entire CD109 open reading frame.

TABLE 2

| Fragment | Sense Primer | | Antisense Primer | Size (bp) | Annealing Temperature (° C.) |
|---|---|---|---|---|---|
| 1 | K1-80<br>5' GTAGCCCAGGCAGACGCC 3'<br>(SEQ ID NO:15) | (-24) | K1-650<br>5' GTGACAACCACTGTTGGATCAA 3'<br>(SEQ ID NO:23) | 544 568 | 59 |

TABLE 2-continued

| Fragment | Sense Primer | | Antisense Primer | | Size (bp) | Annealing Temperature (° C.) |
|---|---|---|---|---|---|---|
| 2 | K1-1<br>5' CGCATTGTTACACTCTTCTC 3'<br>(SEQ ID NO:16) | 445 | K1-1120<br>5' TACATTTCTTGAAATACCTG 3'<br>(SEQ ID NO:24) | 1014 | 570 | 50 |
| 3 | K1-1022<br>5' GATTCTTCAAATGGACTTT 3'<br>(SEQ ID NO:17) | 910 | K1-REV-1<br>5' GGCTGTGTCACAGAGATC 3'<br>(SEQ ID NO:25) | 1747 | 838 | 50 |
| 4 | K1-1400<br>5' TGAATTCCCAATCCTGGAGGA 3'<br>(SEQ ID NO:18) | 1291 | GSP3<br>5' GCCACCCAAGAAGTGATAGA 3'<br>(SEQ ID NO:26) | 2165 | 875 | 55 |
| 5 | K1-M43<br>5' TTCAGGAATGTGGACTCTGG 3'<br>(SEQ ID NO:19) | 1898 | 6R4N<br>5' CGGCTTCAAGGAAACATCT 3'<br>(SEQ ID NO:27) | 2998 | 1101 | 56 |
| 6 | K1-3080<br>5' CTGGGAGCACTTGGTTGTCA 3'<br>(SEQ ID NO:20) | 2948 | 1-5N<br>5' CAGCAACATCTAAATCAAAGGC 3'<br>(SEQ ID NO:28) | 3859 | 912 | 56 |
| 7 | K1-3570<br>5' ACAATTTCAGACTTCTGAGG 3'<br>(SEQ ID NO:21) | 3462 | 7U3N<br>5' CACAGCCAAAGTTCCATA 3'<br>(SEQ ID NO:29) | 4337 | 876 | 50 |
| 8 | K1-3920<br>5' GACGAAGATCTATCCAAAATC 3'<br>(SEQ ID NO:22) | 3812 | K1-4600<br>5' GCTAGGACCTGTTGTACACC 3'<br>(SEQ ID NO:30) | 4489 | 678 | 55 |

Table 2 lists the position of the 5' end of each oligonucleotide with respect to the CD109 cDNA sequence, which includes both 3' and 5' untranslated regions, is noted in parentheses. The CD109 ORF encompasses nucleotides 1-4335 of the published CD109 cDNA, and corresponds exactly to the CD109 cDNA sequence presented in SEQ ID NO:1. The size of each PCR product, and the annealing temperature used for the corresponding primer pair, is listed.

PCR reactions (50:I) containing 1×PCR buffer (Gibco Life Technologies), 1.5 mM MgCl$_2$, 200:M of each dNTP, 1:M of each primer, 1.25 units Taq polymerase (Gibco Life Technologies), and 3:I cDNA underwent 40 cycles of 94° C. (45 seconds), primer-specific annealing temperature (Table 2; 45 seconds), and 72° C. (45-60 seconds), using a Perkin Elmer 2400 thermocycler. PCR products (30:I) were subsequently size-separated electrophoretically on a 1.2% agarose/TAE gel containing 1:g/ml ethidium bromide. Bands were subsequently excised and purified (50:I) using the QIAquick (Qiagen) kit for direct sequencing and subcloning. Sequencing reactions (3-5:I purified product per reaction) were carried out using the Thermosequenase Cy5.5 dye terminator sequencing kit (Amersham Pharmacia Biotech) and the same primers that had been used for initial PCR amplification (Table 2), or selected internal CD109-specific primers as appropriate, and were subsequently analysed using the Open Gene automated DNA sequencing system (Visible Genetics). In parallel, PCR products were cloned into PmeI-digested pMABI, a pBS SK(−) (Stratagene) derivative containing a PmeI restriction site within the polylinker. Resultant plasmid clones were analysed by alkaline lysis/restriction digestion, and as appropriate (and following an additional overnight 13% PEG/ 1.6 M NaCl precipitation), by DNA sequence analysis as above. By combining direct PCR sequencing and the analysis of subcloned fragments, it was ensured that the DNA sequence of each PCR-derived cDNA fragment was obtained independently at least twice, with each fragment being sequenced in both directions in its entirety.

This analysis revealed that the CD109 cDNA sequences of Gov$^{aa}$ and Gov$^{bb}$ individuals differed by a single nucleotide at position 2108 of the sequence shown in SEQ ID NO:1. Gov$^{a/a}$ individuals have an A at position 2108, whereas Gov$^{b/b}$ individuals have a C at the same position. This change results in a Tyr-Ser amino acid polymorphism at residue 703 of the full-length CD109 polypeptide chain. This single nucleotide polymorphism also results in a BstNI restriction site in the Govb allele that is not present in the Gov$^a$ allele. Analysis of the other regions of the CD109 cDNA in their entirety revealed no other nucleotide differences that segregated with Gov phenotype (i.e., that could be used to distinguish the Gov$^a$ allele from the Gov$^b$ allele).

To facilitate subsequent genomic DNA analyses of the Gov$^{a/b}$ alleles, the intron/exon junctions of the exon bearing the putative Gov-specific nucleotide substitution identified above, as well as the DNA sequence of the flanking introns, were determined. CD109 cDNA-specific oligonucleotides binding in the vicinity of this substitution were used for the direct sequencing of p4L10, a pCYPAC_1-derived PAC clone bearing the human CD109 locus using the Open Gene system (Visible Genetics) as above. The nucleotide sequence of the Gov polymorphism-containing exon, as well as of the flanking introns, is presented in SEQ ID NO:5. The Gov polymorphism lies at nucleotide position 954 in SEQ ID NO:5. Subsequent work has mapped the intron-exon structure of the entire human CD109 locus, and has determined that the Gov single nucleotide polymorphism of CD109 lies in exon 19 of the CD109 gene.

EXAMPLE 2

RFLP Analysis of PCR Amplified Genomic DNA

The A-C Gov CD109 polymorphism corresponds to the internal nucleotide of the first complete codon of exon 19 of the CD109 gene. As this exon comprises only 118 nucleotides, and the Gov polymorphism lies almost at the extreme 5' end of this exon, we determined the nucleotide sequence of both introns flanking this exon to facilitate subsequent genomic DNA analyses of the Gov$^{a/b}$ alleles. The DNA sequence of CD109 exon 19 and its flanking introns (CD109 introns 18 and 19) is presented as SEQ ID NO:5. To confirm that the A to C polymorphism at position 2108 of the CD109 open reading frame (nucleotide 2108, SEQ ID NO: 1; nucleotide 954, SEQ ID NO:5) segregates with the Gov phenotype, RFLP analysis was carried out on PCR amplified genomic CD109 DNA using the BstNI restriction endonuclease, which recognises the DNA sequence 5'CCAGG 3' found in the Gov$^b$ cDNA (nucleotides position 2108-2112 in SEQ ID NO:3; the corresponding Gov$^a$ sequence, 5' ACAGG 3', is nucleotides 2108-2112 in SEQ ID NO:1). This enzyme does not cleave at 5' ACAGG 3' (found in Gov$^a$; nucleotides 2108-2112 in SEQ ID NO:1). A 448 bp genomic fragment was PCR-amplified from Gov$^{aa}$, Gov$^{ab}$, and Gov$^{bb}$ individuals using the pair of oligonucleotides SEQ ID NO:9 and SEQ ID NO:10. These oligonucleotides flank exon 19. The former binds within intron 18 (nucleotides 875-892 SEQ ID NO:5), while the latter binds within intron 19 to the sequence complementary to nucleotides 1305-1322 of SEQ ID NO:5). The resultant 448 bp PCR product, when digested with BstNI, yielded the restriction fragments predicted on the basis that the A to C polymorphism at position 2108 (SEQ ID NO:1) segregates with the Gov phenotype.

EXAMPLE 3

Hybridization Analysis of PCR Amplified Genomic DNA

To further confirm that the A to C polymorphism at position 2108 of the CD109 open reading frame (nucleotide 2108, SEQ ID NO:1; nucleotide 954, SEQ ID NO:5) segregates with the Gov phenotype, we also performed an alternative analysis involving the selective hybridization of Gov allele-specific DNA probes to PCR amplified genomic CD109 DNA. Two primers flanking the polymorphic A-C site at position 2108 (SEQ ID NO:1; position 954, SEQ ID NO:5) were designed to amplify by PCR a 105 bp genomic DNA fragment containing the polymorphic site from genomic DNA isolated from Gov$^{aa}$, Gov$^{ab}$, and Gov$^{bb}$ individuals. The first primer (SEQ ID NO:11) binds within intron 18 to nucleotides 902-928 of SEQ ID NO:5. The second primer (SEQ ID NO:12) binds within exon 19 to the sequence complementary to nucleotides 977-1106 of SEQ ID NO:5. Two additional nucleotide probes were designed—one specific for the target sequence of the Gov$^a$ allele of the CD109 gene, and the other for the Gov$^b$ allele of the CD109 gene. The first probe (SEQ ID NO:13) overlaps the CD109 intron 18/exon 19 junction, binds to the Gov$^a$ allele at nucleotides 935-974 of SEQ ID NO:5, and was tagged with the fluorescent dye 6-FAM. The second probe (SEQ ID NO:14), also overlapping the CD109 intron 18/exon 19 junction, binds to the Gov$^b$ allele at the position corresponding to nucleotides 935-971 of SEQ ID NO:5, and was tagged with the fluorescent dye VIC. Genomic DNA was isolated from Gov phenotyped human peripheral blood leukocytes, and PCR/hybridization analysis was carried out using Taqman real-time PCR technology (Perkin Elmer). Genomic DNA was amplified using primers SEQ ID NO:11 and SEQ ID NO:12, with each reaction additionally containing 100 nM FAM-labelled Gov$^a$ probe and 200 nM VIC-labelled Gov$^b$ probe. Allelic discrimination, based on allele-specific fluorescence, was then determined using a post-PCR plate reader (Perkin Elmer). In all cases, PCR/fluorescence-based Gov genotyping correlated with the Gov phenotype, indicating that the A to C polymorphism at position 2108 (SEQ ID NO: 1) does indeed segregate with the Gov phenotype.

EXAMPLE 4

SSP Analysis of PCR Amplified Genomic DNA

To further confirm that the A to C polymorphism at position 2108 of the CD109 open reading frame (nucleotide 2108, SEQ ID NO:1; nucleotide 954, SEQ ID NO:5) segregates with the Gov phenotype, we also performed an alternative analysis involving SSCP analysis of PCR amplified genomic CD109 DNA. Two Gov allele-specific antisense oligonucleotides—SEQ ID NO:6 and SEQ ID NO:7—differing by a single 3' nucleotide (and binding to sequence complementary to nucleotides 954-976 of SEQ ID NO:5, and of the Gov$^b$ counterpart of SEQ ID NO:5, respectively), were combined with a common sense primer—SEQ ID NO:8 binds within intron 18 and which corresponds to nucleotides 752-773 of SEQ ID NO:5, to amplify a 225 bp genomic DNA fragment containing the Gov polymorphic site from genomic DNA isolated from Gov$^{aa}$, Gov$^{ab}$, and Gov$^{bb}$ individuals. In all cases, complete concordance between PCR-SSP analysis and Gov phenotyping was observed.

Sequences:
SEQ ID NO:1 consists of the entire 4335 nucleotide CD109 cDNA open reading frame encoding the Gov$^a$ allele. The Gov$^a$ allele comprises an A at nucleotide position 2108.
SEQ ID NO:2 consists of the entire 1445 aa protein sequence produced from CD109 Gov$^a$ cDNA. The Gov$^a$ allele comprises a Tyr at amino acid 703.
SEQ ID NO:3 consists of the entire 4335 nucleotide CD109 cDNA open reading frame encoding the Gov$^b$ allele. The Gov$^b$ allele comprises a C at nucleotide position 2108.
SEQ ID NO:4 consists of the entire 1445 aa protein sequence produced from the CD109 Gov$^b$ cDNA. The Gov$^b$ allele comprises a Ser at amino acid 703.
SEQ ID NO:5 consists of the CD109 genomic DNA comprising CD109 exon 19 and the flanking introns, introns 18 and 19. The 118 nucleotide exon 19, comprising nucleotides 952-1069 of SEQ ID NO:5, corresponds to nucleotides 2106-2223 of SEQ ID NO:1. The A to C Gov polymorphism of CD109 (corresponding to nucleotide 2108 of SEQ ID NO:1) therefore corresponds to nucleotide 954 of SEQ ID NO:5. In the Gov$^a$ allele, nucleotide 954 is A, while in the Gov$^b$ allele nucleotide 954 is C. Thus, SEQ ID NO:5 corresponds to the Gov$^a$ allele of CD109. Within SEQ ID NO:5, nucleotides 1-951 correspond to CD109 intron 18, while nucleotides 1070-2608 correspond to intron 19.

We note that nucleotides 2108-2112 of SEQ ID NO:1, and the corresponding nucleotides 954-958 of SEQ ID NO:5, which consist of the sequence 5' ACAGG 3' (and which contains the Gov$^a$ allele-specific polymorphic nucleotide at its 5' end), is not cleavable by the restriction endonuclease BstNI. However, in the corresponding Gov$^b$ allele, the corresponding sequence—5' CCAGG 3'—is cleavable by BstNI, and that the two Gov alleles can be discriminated on this basis. We note also that a group of restriction endonucleases—Bst2UI, BstNI, BstOI, EcoRII, MaeIII, MspR91, MvaI, or ScrFI (or one of their isoschizomers)—is capable of differentiating between the Gov$^a$ and Gov$^b$ alleles on this basis.

SEQ ID NO:6-SEQ ID NO:14 comprise oligonucleotides for the PCR amplification of Gov polymorphism containing CD109 sequence from RNA, cDNA derived from RNA, or from genomic DNA, and for the Gov typing analyses of such amplified DNA fragments.

SEQ ID NO:6.

SEQ ID NO:3, an antisense oligonucleotide specific for the Gov$^a$ allele, binds to exon 19 sequence complementary to nucleotides 954-976 of SEQ ID NO:5. SEQ ID NO:6 and SEQ ID NO:7 (see below) differ by a single allele-specific 3' nucleotide

SEQ ID NO:7.

SEQ ID NO:7, an antisense oligonucleotide specific for the Gov$^b$ allele, binds to exon 19 sequence complementary to nucleotides 954-976 of the Gov$^b$ counterpart of SEQ ID NO:5. SEQ ID NO:6 (see above) and SEQ ID NO:7 differ by a single allele-specific 3' nucleotide.

SEQ ID NO:8.

SEQ ID NO:8 binds within intron 18, and corresponds to nucleotides 752-773 of SEQ ID NO:5.

SEQ ID NO:9.

SEQ ID NO:9 binds within intron 18 (nucleotides 875-892 SEQ ID NO:5).

SEQ ID NO:10.

SEQ ID NO:10 binds within intron 19 to the sequence complementary to nucleotides 1305-1322 of SEQ ID NO:5.

SEQ ID NO:11

SEQ ID NO:1 binds within intron 18 to nucleotides 902-928 of SEQ ID NO:5.

SEQ ID NO:12.

SEQ ID NO:12, binds within exon 19 to the sequence complementary to nucleotides 977-1006 of SEQ ID NO:5.

SEQ ID NO:13.

SEQ ID NO:13, specific for the Gov$^a$ allele, overlaps the CD109 intron 18/exon 19 junction, and binds to the Gov$^a$ allele at nucleotides 935-974 of SEQ ID NO:5.

SEQ ID NO:14.

SEQ ID NO:14, specific for the Gov$^b$ allele, overlaps the CD109 intron 18/exon 19 junction, and binds to the Gov$^b$ allele at the position corresponding to nucleotides 935-971 of SEQ ID NO:5.

---

We claim

1. A method of Gov alloantigen genotyping a human subject to determine whether the subject has a $Gov^a$ or $Gov^b$ allele genotype, comprising:
   (a) providing a CD109 nucleic acid sample derived from the subject;
   (b) detecting the nucleotide present in a CD109 nucleic acid at a position corresponding to position 2108 of SEQ ID NO: 1 or SEQ ID NO: 3, wherein the position includes a single nucleotide polymorphism distinctive of a $Gov^a$ or a $Gov^b$ allele; and
   (c) identifying a Gov allele present in said subject based upon the detected nucleotide, wherein the presence of an adenine at the position indicates the $Gov^a$ allele and the presence of a cytosine at the position indicates the $Gov^b$ allele.

2. The method of claim 1 comprising determining whether the subject is homozygous or heterozygous for the $Gov^a$ or $Gov^b$ alleles.

3. The method of claim 2, wherein if the subject is determined to be homozygous for the $Gov^a$ or $Gov^b$ alleles, the subject is at risk of post-transfusion purpura ("PTP"), post-transfusion platelet refractoriness ("PR") or neonatal alloimmune thrombocytopenia ("NAIT") upon transfusion or pregnancy.

4. The method of claim 2, wherein the sample is from a subject that has excessive bleeding and abnormal destruction of blood platelets, wherein if the subject is determined to be homozygous for the $Gov^a$ or $Gov^b$ alleles, the genotyping is indicative of post-transfusion purpura ("PTP"), post-transfusion platelet refractoriness ("PR") or neonatal alloimmune thrombocytopenia ("NAIT").

5. The method of claim 1, wherein the nucleic acid is obtained by amplifying the nucleic acid from the subject.

6. The method of claim 5, wherein the nucleic acid is obtained by amplification with an oligonucleotide that binds specifically to the position corresponding to position 2108 of SEQ ID NO: 1 or SEQ ID NO: 3.

7. The method of claim 1, wherein the nucleic acid is obtained from mRNA from human platelets, T cells, endothelial cells, or human genomic DNA.

8. The method of claim 1, wherein the detection step comprises determining the nucleotide sequence of the CD109 nucleic acid.

9. The method of claim 1, wherein the detection step comprises contacting the nucleic acid with an oligonucleotide that binds specifically to the position corresponding to position 2108 of SEQ ID NO: 1 or SEQ ID NO: 3 under high stringency conditions.

10. The method of claim 9, wherein the oligonucleotide will selectively hybridize to (i) a region of CD109 nucleic acid that includes a single polymorphism distinctive of a $Gov^a$ allele or (ii) a region of CD109 nucleic acid that includes a single polymorphism distinctive of a $Gov^b$ allele.

11. The method of claim 1, wherein the detecting step comprises:
(a) performing a restriction endonuclease digestion of the nucleic acid sample, thereby providing a nucleic acid digest; and
(b) contacting the digest with an oligonucleotide that binds specifically to the position corresponding to position 2108 of SEQ ID NO: 1 or SEQ ID NO: 3 or position 954 of SEQ ID NO: 5.

12. The method of claim 10, wherein the hybridization occurs either during or subsequent to PCR amplification and the analysis is by "Real-Time" PCR analysis, or fluorimetric analysis.

13. The method of claim 1, wherein the detection step comprises:
(a) incubation of the CD109 nucleic acid with a restriction endonuclease under conditions whereby the DNA will be cleaved if the nucleic acid comprises a recognition site for the enzyme; and
(b) determining whether the nucleic acid contains a recognition site for the restriction enzyme characteristic of cDNA made from mRNA encoding a $Gov^a$ or $Gov^b$ allele of CD109.

14. The method of claim 13, wherein the restriction enzyme is selected from the group consisting of Bst2UI, BstNI, BstOI, EcoRII, MaeIII, MspR91, MvaI, ScrFI or an isoschizomer thereof.

15. The method of claim 13, wherein the determination step includes size analysis of the nucleic acid.

16. The method of claim 13, wherein the amplified nucleic acid is analyzed by electrophoretic mobility and the mobility of the amplified nucleic acid is compared to the characteristic mobility of amplified nucleic acid fragments corresponding to the $Gov^a$ or $Gov^b$ alleles of CD109.

17. A method of amplifying CD109 mRNA comprising amplifying the mRNA by PCR using an oligonucleotide comprising a sequence which binds specifically to (i) a region of CD109 nucleic acid that includes a single nucleotide polymorphism that is distinctive of a $Gov^a$ allele and/or (ii) a region of CD109 nucleic acid that includes a single nucleotide polymorphism that is distinctive of a $Gov^b$ allele, wherein the oligonucleotide binds specifically to the CD109 at position 2108 of SEQ ID NO: 1 or SEQ ID NO: 3 or position 954 of SEQ ID NO: 5, wherein said oligonucleotide consists of 8 to 50 nucleotides.

18. The method of claim 1, wherein the adenosine or cytosine nucleotide is detected in genomic DNA, wherein in the genomic DNA position 954 of SEQ ID NO: 5 is in a location corresponding to position 2108 of SEQ ID NOS: 1 and 3, wherein the $Gov^a$ allele comprises an A at a position corresponding to position 954 of SEQ ID NO: 5 and the $Gov^b$ allele comprises a C at a position corresponding to position 954 of SEQ ID NO: 5.

19. The method of claim 1, wherein the CD109 nucleic acid sample comprises nucleic acids that represent the subject's two alleles of the $Gov^a$/$Gov^b$ biallelic system and wherein i) detecting the presence of only A at the position indicates that the subject is homozygous for $Gov^a$, ii) detecting the presence of only C indicates that the subject is homozygous for $Gov^b$ and iii) detecting the presence of A and C indicates that the subject is heterozygous.

20. The method of claim 6, wherein the oligonucleotide contains guanine or thymine at a position complementary to nucleotide position 2108.

* * * * *

SEQUENCE LISTING

```
<160> NUMBER OF SEQ ID NOS: 30

<210> SEQ ID NO 1
<211> LENGTH: 4335
<212> TYPE: DNA
<213> ORGANISM: HUMAN
<220> FEATURE:
<221> NAME/KEY: CDS
<222> LOCATION: (1)..(4335)

<400> SEQUENCE: 1 atg cag ggc cca ccg ctc ctg acc gcc gcc cac ctc ctc tgc gtg tgc      48
Met Gln Gly Pro Pro Leu Leu Thr Ala Ala His Leu Leu Cys Val Cys
1               5                   10                  15 acc gcc gcg ctg gcc gtg gct ccc ggg cct cgg ttt ctg gtg aca gcc      96
Thr Ala Ala Leu Ala Val Ala Pro Gly Pro Arg Phe Leu Val Thr Ala
                20                  25                  30 cca ggg atc atc agg ccc gga gga aat gtg act att ggg gtg gag ctt     144
Pro Gly Ile Ile Arg Pro Gly Gly Asn Val Thr Ile Gly Val Glu Leu
            35                  40                  45 ctg gaa cac tgc cct tca cag gtg act gtg aag gcg gag ctc ctc aag     192
Leu Glu His Cys Pro Ser Gln Val Thr Val Lys Ala Glu Leu Leu Lys
        50                  55                  60 aca gca tca aac ctc act gtc tct gtc ctg gaa gca gaa gga gtc ttt     240
Thr Ala Ser Asn Leu Thr Val Ser Val Leu Glu Ala Glu Gly Val Phe
65                  70                  75                  80 gaa aaa ggc tct ttt aag aca ctt act ctt cca tca cta cct ctg aac     288
Glu Lys Gly Ser Phe Lys Thr Leu Thr Leu Pro Ser Leu Pro Leu Asn
                85                  90                  95 agt gca gat gag att tat gag cta cgt gta acc gga cgt acc cag gat     336
Ser Ala Asp Glu Ile Tyr Glu Leu Arg Val Thr Gly Arg Thr Gln Asp
                100                 105                 110 gag att tta ttc tct aat agt acc cgc tta tca ttt gag acc aag aga     384
Glu Ile Leu Phe Ser Asn Ser Thr Arg Leu Ser Phe Glu Thr Lys Arg
```

-continued

```
                115                 120                 125
ata tct gtc ttc att caa aca gac aag gcc tta tac aag cca aag caa      432
Ile Ser Val Phe Ile Gln Thr Asp Lys Ala Leu Tyr Lys Pro Lys Gln
130                 135                 140 gaa gtg aag ttt cgc att gtt aca ctc ttc tca gat ttt aag cct tac      480
Glu Val Lys Phe Arg Ile Val Thr Leu Phe Ser Asp Phe Lys Pro Tyr
145                 150                 155                 160 aaa acc tct tta aac att ctc att aag gac ccc aaa tca aat ttg atc      528
Lys Thr Ser Leu Asn Ile Leu Ile Lys Asp Pro Lys Ser Asn Leu Ile
                165                 170                 175 caa cag tgg ttg tca caa caa agt gat ctt gga gtc att tcc aaa act      576
Gln Gln Trp Leu Ser Gln Gln Ser Asp Leu Gly Val Ile Ser Lys Thr
            180                 185                 190 ttt cag cta tct tcc cat cca ata ctt ggt gac tgg tct att caa gtt      624
Phe Gln Leu Ser Ser His Pro Ile Leu Gly Asp Trp Ser Ile Gln Val
        195                 200                 205 caa gtg aat gac cag aca tat tat caa tca ttt cag gtt tca gaa tat      672
Gln Val Asn Asp Gln Thr Tyr Tyr Gln Ser Phe Gln Val Ser Glu Tyr
    210                 215                 220 gta tta cca aaa ttt gaa gtg act ttg cag aca cca tta tat tgt tct      720
Val Leu Pro Lys Phe Glu Val Thr Leu Gln Thr Pro Leu Tyr Cys Ser
225                 230                 235                 240 atg aat tct aag cat tta aat ggt acc atc acg gca aag tat aca tat      768
Met Asn Ser Lys His Leu Asn Gly Thr Ile Thr Ala Lys Tyr Thr Tyr
                245                 250                 255 ggg aag cca gtg aaa gga gac gta acg ctt aca ttt tta cct tta tcc      816
Gly Lys Pro Val Lys Gly Asp Val Thr Leu Thr Phe Leu Pro Leu Ser
            260                 265                 270 ttt tgg gga aag aag aaa aat att aca aaa aca ttt aag ata aat gga      864
Phe Trp Gly Lys Lys Lys Asn Ile Thr Lys Thr Phe Lys Ile Asn Gly
        275                 280                 285 tct gca aac ttc tct ttt aat gat gaa gag atg aaa aat gta atg gat      912
Ser Ala Asn Phe Ser Phe Asn Asp Glu Glu Met Lys Asn Val Met Asp
    290                 295                 300 tct tca aat gga ctt tct gaa tac ctg gat cta tct tcc cct gga cca      960
Ser Ser Asn Gly Leu Ser Glu Tyr Leu Asp Leu Ser Ser Pro Gly Pro
305                 310                 315                 320 gta gaa att tta acc aca gtg aca gaa tca gtt aca ggt att tca aga     1008
Val Glu Ile Leu Thr Thr Val Thr Glu Ser Val Thr Gly Ile Ser Arg
                325                 330                 335 aat gta agc act aat gtg ttc ttc aag caa cat gat tac atc att gag     1056
Asn Val Ser Thr Asn Val Phe Phe Lys Gln His Asp Tyr Ile Ile Glu
            340                 345                 350 ttt ttt gat tat act act gtc ttg aag cca tct ctc aac ttc aca gcc     1104
Phe Phe Asp Tyr Thr Thr Val Leu Lys Pro Ser Leu Asn Phe Thr Ala
        355                 360                 365 act gtg aag gta act cgt gct gat ggc aac caa ctg act ctt gaa gaa     1152
Thr Val Lys Val Thr Arg Ala Asp Gly Asn Gln Leu Thr Leu Glu Glu
    370                 375                 380 aga aga aat aat gta gtc ata aca gtg aca cag aga aac tat act gag     1200
Arg Arg Asn Asn Val Val Ile Thr Val Thr Gln Arg Asn Tyr Thr Glu
385                 390                 395                 400 tac tgg agc gga tct aac agt gga aat cag aaa atg gaa gct gtt cag     1248
Tyr Trp Ser Gly Ser Asn Ser Gly Asn Gln Lys Met Glu Ala Val Gln
                405                 410                 415 aaa ata aat tat act gtc ccc caa agt gga act ttt aag att gaa ttc     1296
Lys Ile Asn Tyr Thr Val Pro Gln Ser Gly Thr Phe Lys Ile Glu Phe
            420                 425                 430 cca atc ctg gag gat tcc agt gag cta cag ttg aag gcc tat ttc ctt     1344
```

```
                Pro Ile Leu Glu Asp Ser Ser Glu Leu Gln Leu Lys Ala Tyr Phe Leu
                        435                 440                 445 ggt agt aaa agt agc atg gca gtt cat agt ctg ttt aag tct cct agt         1392
Gly Ser Lys Ser Ser Met Ala Val His Ser Leu Phe Lys Ser Pro Ser
450                 455                 460 aag aca tac atc caa cta aaa aca aga gat gaa aat ata aag gtg gga         1440
Lys Thr Tyr Ile Gln Leu Lys Thr Arg Asp Glu Asn Ile Lys Val Gly
465                 470                 475                 480 tcg cct ttt gag ttg gtg gtt agt ggc aac aaa cga ttg aag gag tta         1488
Ser Pro Phe Glu Leu Val Val Ser Gly Asn Lys Arg Leu Lys Glu Leu
                485                 490                 495 agc tat atg gta gta tcc agg gga cag ttg gtg gct gta gga aaa caa         1536
Ser Tyr Met Val Val Ser Arg Gly Gln Leu Val Ala Val Gly Lys Gln
                500                 505                 510 aat tca aca atg ttc tct tta aca cca gaa aat tct tgg act cca aaa         1584
Asn Ser Thr Met Phe Ser Leu Thr Pro Glu Asn Ser Trp Thr Pro Lys
            515                 520                 525 gcc tgt gta att gtg tat tat att gaa gat gat ggg gaa att ata agt         1632
Ala Cys Val Ile Val Tyr Tyr Ile Glu Asp Asp Gly Glu Ile Ile Ser
        530                 535                 540 gat gtt cta aaa att cct gtt cag ctt gtt ttt aaa aat aag ata aag         1680
Asp Val Leu Lys Ile Pro Val Gln Leu Val Phe Lys Asn Lys Ile Lys
545                 550                 555                 560 cta tat tgg agt aaa gtg aaa gct gaa cca tct gag aaa gtc tct ctt         1728
Leu Tyr Trp Ser Lys Val Lys Ala Glu Pro Ser Glu Lys Val Ser Leu
                565                 570                 575 agg atc tct gtg aca cag cct gac tcc ata gtt ggg att gta gct gtt         1776
Arg Ile Ser Val Thr Gln Pro Asp Ser Ile Val Gly Ile Val Ala Val
                580                 585                 590 gac aaa agt gtg aat ctg atg aat gcc tct aat gat att aca atg gaa         1824
Asp Lys Ser Val Asn Leu Met Asn Ala Ser Asn Asp Ile Thr Met Glu
            595                 600                 605 aat gtg gtc cat gag ttg gaa ctt tat aac aca gga tat tat tta ggc         1872
Asn Val Val His Glu Leu Glu Leu Tyr Asn Thr Gly Tyr Tyr Leu Gly
        610                 615                 620 atg ttc atg aat tct ttt gca gtc ttt cag gaa tgt gga ctc tgg gta         1920
Met Phe Met Asn Ser Phe Ala Val Phe Gln Glu Cys Gly Leu Trp Val
625                 630                 635                 640 ttg aca gat gca aac ctc acg aag gat tat att gat ggt gtt tat gac         1968
Leu Thr Asp Ala Asn Leu Thr Lys Asp Tyr Ile Asp Gly Val Tyr Asp
                645                 650                 655 aat gca gaa tat gct gag agg ttt atg gag gaa aat gaa gga cat att         2016
Asn Ala Glu Tyr Ala Glu Arg Phe Met Glu Glu Asn Glu Gly His Ile
                660                 665                 670 gta gat att cat gac ttt tct ttg ggt agc agt cca cat gtc cga aag         2064
Val Asp Ile His Asp Phe Ser Leu Gly Ser Ser Pro His Val Arg Lys
            675                 680                 685 cat ttt cca gag act tgg att tgg cta gac acc aac atg ggt tac agg         2112
His Phe Pro Glu Thr Trp Ile Trp Leu Asp Thr Asn Met Gly Tyr Arg
        690                 695                 700 att tac caa gaa ttt gaa gta act gta cct gat tct atc act tct tgg         2160
Ile Tyr Gln Glu Phe Glu Val Thr Val Pro Asp Ser Ile Thr Ser Trp
705                 710                 715                 720 gtg gct act ggt ttt gtg atc tct gag gac ctg ggt ctt gga cta aca         2208
Val Ala Thr Gly Phe Val Ile Ser Glu Asp Leu Gly Leu Gly Leu Thr
                725                 730                 735 act act cca gtg gag ctc caa gcc ttc caa cca ttt ttc att ttt ttg         2256
Thr Thr Pro Val Glu Leu Gln Ala Phe Gln Pro Phe Phe Ile Phe Leu
                740                 745                 750
```

```
aat ctt ccc tac tct gtt atc aga ggt gaa gaa ttt gct ttg gaa ata         2304
Asn Leu Pro Tyr Ser Val Ile Arg Gly Glu Glu Phe Ala Leu Glu Ile
        755                 760                 765 act ata ttc aat tat ttg aaa gat gcc act gag gtt aag gta atc att         2352
Thr Ile Phe Asn Tyr Leu Lys Asp Ala Thr Glu Val Lys Val Ile Ile
    770                 775                 780 gag aaa agt gac aaa ttt gat att cta atg act tca aat gaa ata aat         2400
Glu Lys Ser Asp Lys Phe Asp Ile Leu Met Thr Ser Asn Glu Ile Asn
785                 790                 795                 800 gcc aca ggc cac cag cag acc ctt ctg gtt ccc agt gag gat ggg gca         2448
Ala Thr Gly His Gln Gln Thr Leu Leu Val Pro Ser Glu Asp Gly Ala
                805                 810                 815 act gtt ctt ttt ccc atc agg cca aca cat ctg gga gaa att cct atc         2496
Thr Val Leu Phe Pro Ile Arg Pro Thr His Leu Gly Glu Ile Pro Ile
            820                 825                 830 aca gtc aca gct ctt tca ccc act gct tct gat gct gtc acc cag atg         2544
Thr Val Thr Ala Leu Ser Pro Thr Ala Ser Asp Ala Val Thr Gln Met
        835                 840                 845 att tta gta aag gct gaa gga ata gaa aaa tca tat tca caa tcc atc         2592
Ile Leu Val Lys Ala Glu Gly Ile Glu Lys Ser Tyr Ser Gln Ser Ile
    850                 855                 860 tta tta gac ttg act gac aat agg cta cag agt acc ctg aaa act ttg         2640
Leu Leu Asp Leu Thr Asp Asn Arg Leu Gln Ser Thr Leu Lys Thr Leu
865                 870                 875                 880 agt ttc tca ttt cct cct aat aca gtg act ggc agt gaa aga gtt cag         2688
Ser Phe Ser Phe Pro Pro Asn Thr Val Thr Gly Ser Glu Arg Val Gln
                885                 890                 895 atc act gca att gga gat gtt ctt ggt cct tcc atc aat ggc tta gcc         2736
Ile Thr Ala Ile Gly Asp Val Leu Gly Pro Ser Ile Asn Gly Leu Ala
            900                 905                 910 tca ttg att cgg atg cct tat ggc tgt ggt gaa cag aac atg ata aat         2784
Ser Leu Ile Arg Met Pro Tyr Gly Cys Gly Glu Gln Asn Met Ile Asn
        915                 920                 925 ttt gct cca aat att tac att ttg gat tat ctg act aaa aag aaa caa         2832
Phe Ala Pro Asn Ile Tyr Ile Leu Asp Tyr Leu Thr Lys Lys Lys Gln
    930                 935                 940 ctg aca gat aat ttg aaa gaa aaa gct ctt tca ttt atg agg caa ggt         2880
Leu Thr Asp Asn Leu Lys Glu Lys Ala Leu Ser Phe Met Arg Gln Gly
945                 950                 955                 960 tac cag aga gaa ctt ctc tat cag agg gaa gat ggc tct ttc agt gct         2928
Tyr Gln Arg Glu Leu Leu Tyr Gln Arg Glu Asp Gly Ser Phe Ser Ala
                965                 970                 975 ttt ggg aat tat gac cct tct ggg agc act tgg ttg tca gct ttt gtt         2976
Phe Gly Asn Tyr Asp Pro Ser Gly Ser Thr Trp Leu Ser Ala Phe Val
            980                 985                 990 tta aga tgt ttc ctt gaa gcc gat    cct tac ata gat att    gat cag aat   3024
Leu Arg Cys Phe Leu Glu Ala Asp    Pro Tyr Ile Asp Ile    Asp Gln Asn
        995                 1000                 1005 gtg tta cac aga aca tac act tgg ctt aaa gga cat    cag aaa tcc          3069
Val Leu His Arg Thr Tyr Thr Trp Leu Lys Gly His    Gln Lys Ser
    1010                1015                     1020 aac ggt gaa ttt tgg gat cca gga aga gtg att cat    agt gag ctt          3114
Asn Gly Glu Phe Trp Asp Pro Gly Arg Val Ile His    Ser Glu Leu
1025                1030                         1035 caa ggt ggc aat aaa agt cca gta aca ctt aca gcc    tat att gta          3159
Gln Gly Gly Asn Lys Ser Pro Val Thr Leu Thr Ala    Tyr Ile Val
    1040                1045                     1050 act tct ctc ctg gga tat aga aag tat cag cct aac    att gat gtg          3204
Thr Ser Leu Leu Gly Tyr Arg Lys Tyr Gln Pro Asn    Ile Asp Val
    1055                1060                     1065
```

-continued

| | | |
|---|---|---|
| caa gag tct atc cat ttt ttg gag tct gaa ttc agt aga gga att<br>Gln Glu Ser Ile His Phe Leu Glu Ser Glu Phe Ser Arg Gly Ile<br>1070                    1075                    1080 | 3249 |
| tca gac aat tat act cta gcc ctt ata act tat gca ttg tca tca<br>Ser Asp Asn Tyr Thr Leu Ala Leu Ile Thr Tyr Ala Leu Ser Ser<br>1085                    1090                    1095 | 3294 |
| gtg ggg agt cct aaa gcg aag gaa gct ttg aat atg ctg act tgg<br>Val Gly Ser Pro Lys Ala Lys Glu Ala Leu Asn Met Leu Thr Trp<br>1100                    1105                    1110 | 3339 |
| aga gca gaa caa gaa ggt ggc atg caa ttc tgg gtg tca tca gag<br>Arg Ala Glu Gln Glu Gly Gly Met Gln Phe Trp Val Ser Ser Glu<br>1115                    1120                    1125 | 3384 |
| tcc aaa ctt tct gac tcc tgg cag cca cgc tcc ctg gat att gaa<br>Ser Lys Leu Ser Asp Ser Trp Gln Pro Arg Ser Leu Asp Ile Glu<br>1130                    1135                    1140 | 3429 |
| gtt gca gcc tat gca ctg ctc tca cac ttc tta caa ttt cag act<br>Val Ala Ala Tyr Ala Leu Leu Ser His Phe Leu Gln Phe Gln Thr<br>1145                    1150                    1155 | 3474 |
| tct gag gga atc cca att atg agg tgg cta agc agg caa aga aat<br>Ser Glu Gly Ile Pro Ile Met Arg Trp Leu Ser Arg Gln Arg Asn<br>1160                    1165                    1170 | 3519 |
| agc ttg ggt ggt ttt gca tct act cag gat acc act gtg gct tta<br>Ser Leu Gly Gly Phe Ala Ser Thr Gln Asp Thr Thr Val Ala Leu<br>1175                    1180                    1185 | 3564 |
| aag gct ctg tct gaa ttt gca gcc cta atg aat aca gaa agg aca<br>Lys Ala Leu Ser Glu Phe Ala Ala Leu Met Asn Thr Glu Arg Thr<br>1190                    1195                    1200 | 3609 |
| aat atc caa gtg acc gtg acg ggg cct agc tca cca agt cct gta<br>Asn Ile Gln Val Thr Val Thr Gly Pro Ser Ser Pro Ser Pro Val<br>1205                    1210                    1215 | 3654 |
| aag ttt ctg att gac aca cac aac cgc tta ctc ctt cag aca gca<br>Lys Phe Leu Ile Asp Thr His Asn Arg Leu Leu Leu Gln Thr Ala<br>1220                    1225                    1230 | 3699 |
| gag ctt gct gtg gta cag cca atg gca gtt aat att tcc gca aat<br>Glu Leu Ala Val Val Gln Pro Met Ala Val Asn Ile Ser Ala Asn<br>1235                    1240                    1245 | 3744 |
| ggt ttt gga ttt gct att tgt cag ctc aat gtt gta tat aat gtg<br>Gly Phe Gly Phe Ala Ile Cys Gln Leu Asn Val Val Tyr Asn Val<br>1250                    1255                    1260 | 3789 |
| aag gct tct ggg tct tct aga aga cga aga tct atc caa aat caa<br>Lys Ala Ser Gly Ser Ser Arg Arg Arg Arg Ser Ile Gln Asn Gln<br>1265                    1270                    1275 | 3834 |
| gaa gcc ttt gat tta gat gtt gct gta aaa gaa aat aaa gat gat<br>Glu Ala Phe Asp Leu Asp Val Ala Val Lys Glu Asn Lys Asp Asp<br>1280                    1285                    1290 | 3879 |
| ctc aat cat gtg gat ttg aat gtg tgt aca agc ttt tcg ggc ccg<br>Leu Asn His Val Asp Leu Asn Val Cys Thr Ser Phe Ser Gly Pro<br>1295                    1300                    1305 | 3924 |
| ggt agg agt ggc atg gct ctt atg gaa gtt aac cta tta agt ggc<br>Gly Arg Ser Gly Met Ala Leu Met Glu Val Asn Leu Leu Ser Gly<br>1310                    1315                    1320 | 3969 |
| ttt atg gtg cct tca gaa gca att tct ctg agc gag aca gtg aag<br>Phe Met Val Pro Ser Glu Ala Ile Ser Leu Ser Glu Thr Val Lys<br>1325                    1330                    1335 | 4014 |
| aaa gtg gaa tat gat cat gga aaa ctc aac ctc tat tta gat tct<br>Lys Val Glu Tyr Asp His Gly Lys Leu Asn Leu Tyr Leu Asp Ser<br>1340                    1345                    1350 | 4059 |
| gta aat gaa acc cag ttt tgt gtt aat att cct gct gtg aga aac<br>Val Asn Glu Thr Gln Phe Cys Val Asn Ile Pro Ala Val Arg Asn | 4104 |

-continued

```
         1355                1360                1365
ttt aaa  gtt tca  aat acc  caa gat  gct tca  gtg tcc  ata gtg  gat         4149
Phe Lys  Val Ser  Asn Thr  Gln Asp  Ala Ser  Val Ser  Ile Val  Asp
    1370              1375              1380 tac tat  gag cca  agg aga  cag gcg  gtg aga  agt tac  aac tct  gaa         4194
Tyr Tyr  Glu Pro  Arg Arg  Gln Ala  Val Arg  Ser Tyr  Asn Ser  Glu
    1385              1390              1395 gtg aag  ctg tcc  tcc tgt  gac ctt  tgc agt  gat gtc  cag ggc  tgc         4239
Val Lys  Leu Ser  Ser Cys  Asp Leu  Cys Ser  Asp Val  Gln Gly  Cys
    1400              1405              1410 cgt cct  tgt gag  gat gga  gct tca  ggc tcc  cat cat  cac tct  tca         4284
Arg Pro  Cys Glu  Asp Gly  Ala Ser  Gly Ser  His His  His Ser  Ser
    1415              1420              1425 gtc att  ttt att  ttc tgt  ttc aag  ctt ctg  tac ttt  atg gaa  ctt         4329
Val Ile  Phe Ile  Phe Cys  Phe Lys  Leu Leu  Tyr Phe  Met Glu  Leu
    1430              1435              1440 tgg ctg                                                                    4335
Trp Leu
    1445

<210> SEQ ID NO 2
<211> LENGTH: 1445
<212> TYPE: PRT
<213> ORGANISM: HUMAN

<400> SEQUENCE: 2

Met Gln Gly Pro Pro Leu Leu Thr Ala Ala His Leu Leu Cys Val Cys
1               5                   10                  15

Thr Ala Ala Leu Ala Val Ala Pro Gly Pro Arg Phe Leu Val Thr Ala
                20                  25                  30

Pro Gly Ile Ile Arg Pro Gly Gly Asn Val Thr Ile Gly Val Glu Leu
            35                  40                  45

Leu Glu His Cys Pro Ser Gln Val Thr Val Lys Ala Glu Leu Leu Lys
        50                  55                  60

Thr Ala Ser Asn Leu Thr Val Ser Val Leu Glu Ala Glu Gly Val Phe
65                  70                  75                  80

Glu Lys Gly Ser Phe Lys Thr Leu Thr Leu Pro Ser Leu Pro Leu Asn
                85                  90                  95

Ser Ala Asp Glu Ile Tyr Glu Leu Arg Val Thr Gly Arg Thr Gln Asp
            100                 105                 110

Glu Ile Leu Phe Ser Asn Ser Thr Arg Leu Ser Phe Glu Thr Lys Arg
        115                 120                 125

Ile Ser Val Phe Ile Gln Thr Asp Lys Ala Leu Tyr Lys Pro Lys Gln
    130                 135                 140

Glu Val Lys Phe Arg Ile Val Thr Leu Phe Ser Asp Phe Lys Pro Tyr
145                 150                 155                 160

Lys Thr Ser Leu Asn Ile Leu Ile Lys Asp Pro Lys Ser Asn Leu Ile
                165                 170                 175

Gln Gln Trp Leu Ser Gln Gln Ser Asp Leu Gly Val Ile Ser Lys Thr
            180                 185                 190

Phe Gln Leu Ser Ser His Pro Ile Leu Gly Asp Trp Ser Ile Gln Val
        195                 200                 205

Gln Val Asn Asp Gln Thr Tyr Tyr Gln Ser Phe Gln Val Ser Glu Tyr
    210                 215                 220

Val Leu Pro Lys Phe Glu Val Thr Leu Gln Thr Pro Leu Tyr Cys Ser
225                 230                 235                 240
```

-continued

```
Met Asn Ser Lys His Leu Asn Gly Thr Ile Thr Ala Lys Tyr Thr Tyr
                245                 250                 255
Gly Lys Pro Val Lys Gly Asp Val Thr Leu Thr Phe Leu Pro Leu Ser
            260                 265                 270
Phe Trp Gly Lys Lys Asn Ile Thr Lys Thr Phe Lys Ile Asn Gly
        275                 280                 285
Ser Ala Asn Phe Ser Phe Asn Asp Glu Glu Met Lys Asn Val Met Asp
290                 295                 300
Ser Ser Asn Gly Leu Ser Glu Tyr Leu Asp Leu Ser Ser Pro Gly Pro
305                 310                 315                 320
Val Glu Ile Leu Thr Thr Val Thr Glu Ser Val Thr Gly Ile Ser Arg
                325                 330                 335
Asn Val Ser Thr Asn Val Phe Phe Lys Gln His Asp Tyr Ile Ile Glu
                340                 345                 350
Phe Phe Asp Tyr Thr Thr Val Leu Lys Pro Ser Leu Asn Phe Thr Ala
            355                 360                 365
Thr Val Lys Val Thr Arg Ala Asp Gly Asn Gln Leu Thr Leu Glu Glu
        370                 375                 380
Arg Arg Asn Asn Val Val Ile Thr Val Thr Gln Arg Asn Tyr Thr Glu
385                 390                 395                 400
Tyr Trp Ser Gly Ser Asn Ser Gly Asn Gln Lys Met Glu Ala Val Gln
                405                 410                 415
Lys Ile Asn Tyr Thr Val Pro Gln Ser Gly Thr Phe Lys Ile Glu Phe
                420                 425                 430
Pro Ile Leu Glu Asp Ser Ser Glu Leu Gln Leu Lys Ala Tyr Phe Leu
            435                 440                 445
Gly Ser Lys Ser Ser Met Ala Val His Ser Leu Phe Lys Ser Pro Ser
450                 455                 460
Lys Thr Tyr Ile Gln Leu Lys Thr Arg Asp Glu Asn Ile Lys Val Gly
465                 470                 475                 480
Ser Pro Phe Glu Leu Val Val Ser Gly Asn Lys Arg Leu Lys Glu Leu
                485                 490                 495
Ser Tyr Met Val Val Ser Arg Gly Gln Leu Val Ala Val Gly Lys Gln
                500                 505                 510
Asn Ser Thr Met Phe Ser Leu Thr Pro Glu Asn Ser Trp Thr Pro Lys
            515                 520                 525
Ala Cys Val Ile Val Tyr Tyr Ile Glu Asp Asp Gly Glu Ile Ile Ser
        530                 535                 540
Asp Val Leu Lys Ile Pro Val Gln Leu Val Phe Lys Asn Lys Ile Lys
545                 550                 555                 560
Leu Tyr Trp Ser Lys Val Lys Ala Glu Pro Ser Glu Lys Val Ser Leu
                565                 570                 575
Arg Ile Ser Val Thr Gln Pro Asp Ser Ile Val Gly Ile Val Ala Val
                580                 585                 590
Asp Lys Ser Val Asn Leu Met Asn Ala Ser Asn Asp Ile Thr Met Glu
            595                 600                 605
Asn Val Val His Glu Leu Glu Leu Tyr Asn Thr Gly Tyr Tyr Leu Gly
        610                 615                 620
Met Phe Met Asn Ser Phe Ala Val Phe Gln Glu Cys Gly Leu Trp Val
625                 630                 635                 640
Leu Thr Asp Ala Asn Leu Thr Lys Asp Tyr Ile Asp Gly Val Tyr Asp
                645                 650                 655
Asn Ala Glu Tyr Ala Glu Arg Phe Met Glu Glu Asn Glu Gly His Ile
```

-continued

```
            660                 665                 670
Val Asp Ile His Asp Phe Ser Leu Gly Ser Ser Pro His Val Arg Lys
        675                 680                 685
His Phe Pro Glu Thr Trp Ile Trp Leu Asp Thr Asn Met Gly Tyr Arg
        690                 695                 700
Ile Tyr Gln Glu Phe Glu Val Thr Val Pro Asp Ser Ile Thr Ser Trp
705                 710                 715                 720
Val Ala Thr Gly Phe Val Ile Ser Glu Asp Leu Gly Leu Gly Leu Thr
                725                 730                 735
Thr Thr Pro Val Glu Leu Gln Ala Phe Gln Pro Phe Ile Phe Leu
        740                 745                 750
Asn Leu Pro Tyr Ser Val Ile Arg Gly Glu Glu Phe Ala Leu Glu Ile
        755                 760                 765
Thr Ile Phe Asn Tyr Leu Lys Asp Ala Thr Glu Val Lys Val Ile Ile
        770                 775                 780
Glu Lys Ser Asp Lys Phe Asp Ile Leu Met Thr Ser Asn Glu Ile Asn
785                 790                 795                 800
Ala Thr Gly His Gln Gln Thr Leu Leu Val Pro Ser Glu Asp Gly Ala
                805                 810                 815
Thr Val Leu Phe Pro Ile Arg Pro Thr His Leu Gly Glu Ile Pro Ile
                820                 825                 830
Thr Val Thr Ala Leu Ser Pro Thr Ala Ser Asp Ala Val Thr Gln Met
                835                 840                 845
Ile Leu Val Lys Ala Glu Gly Ile Glu Lys Ser Tyr Ser Gln Ser Ile
        850                 855                 860
Leu Leu Asp Leu Thr Asp Asn Arg Leu Gln Ser Thr Leu Lys Thr Leu
865                 870                 875                 880
Ser Phe Ser Phe Pro Pro Asn Thr Val Thr Gly Ser Glu Arg Val Gln
                885                 890                 895
Ile Thr Ala Ile Gly Asp Val Leu Gly Pro Ser Ile Asn Gly Leu Ala
                900                 905                 910
Ser Leu Ile Arg Met Pro Tyr Gly Cys Gly Glu Gln Asn Met Ile Asn
                915                 920                 925
Phe Ala Pro Asn Ile Tyr Ile Leu Asp Tyr Leu Thr Lys Lys Lys Gln
        930                 935                 940
Leu Thr Asp Asn Leu Lys Glu Lys Ala Leu Ser Phe Met Arg Gln Gly
945                 950                 955                 960
Tyr Gln Arg Glu Leu Leu Tyr Gln Arg Glu Asp Gly Ser Phe Ser Ala
                965                 970                 975
Phe Gly Asn Tyr Asp Pro Ser Gly Ser Thr Trp Leu Ser Ala Phe Val
                980                 985                 990
Leu Arg Cys Phe Leu Glu Ala Asp  Pro Tyr Ile Asp Ile  Asp Gln Asn
        995                 1000                1005
Val Leu His Arg Thr Tyr Thr  Trp Leu Lys Gly His  Gln Lys Ser
        1010                1015                1020
Asn Gly  Glu Phe Trp Asp Pro  Gly Arg Val Ile His  Ser Glu Leu
        1025                1030                1035
Gln Gly  Gly Asn Lys Ser Pro  Val Thr Leu Thr Ala  Tyr Ile Val
        1040                1045                1050
Thr Ser  Leu Leu Gly Tyr Arg  Lys Tyr Gln Pro Asn  Ile Asp Val
        1055                1060                1065
Gln Glu  Ser Ile His Phe Leu  Glu Ser Glu Phe Ser  Arg Gly Ile
        1070                1075                1080
```

```
Ser Asp Asn Tyr Thr Leu Ala Leu Ile Thr Tyr Ala Leu Ser Ser
    1085                1090                1095

Val Gly Ser Pro Lys Ala Lys Glu Ala Leu Asn Met Leu Thr Trp
    1100                1105                1110

Arg Ala Glu Gln Glu Gly Gly Met Gln Phe Trp Val Ser Ser Glu
    1115                1120                1125

Ser Lys Leu Ser Asp Ser Trp Gln Pro Arg Ser Leu Asp Ile Glu
    1130                1135                1140

Val Ala Ala Tyr Ala Leu Leu Ser His Phe Leu Gln Phe Gln Thr
    1145                1150                1155

Ser Glu Gly Ile Pro Ile Met Arg Trp Leu Ser Arg Gln Arg Asn
    1160                1165                1170

Ser Leu Gly Gly Phe Ala Ser Thr Gln Asp Thr Thr Val Ala Leu
    1175                1180                1185

Lys Ala Leu Ser Glu Phe Ala Ala Leu Met Asn Thr Glu Arg Thr
    1190                1195                1200

Asn Ile Gln Val Thr Val Thr Gly Pro Ser Ser Pro Ser Pro Val
    1205                1210                1215

Lys Phe Leu Ile Asp Thr His Asn Arg Leu Leu Leu Gln Thr Ala
    1220                1225                1230

Glu Leu Ala Val Val Gln Pro Met Ala Val Asn Ile Ser Ala Asn
    1235                1240                1245

Gly Phe Gly Phe Ala Ile Cys Gln Leu Asn Val Val Tyr Asn Val
    1250                1255                1260

Lys Ala Ser Gly Ser Ser Arg Arg Arg Ser Ile Gln Asn Gln
    1265                1270                1275

Glu Ala Phe Asp Leu Asp Val Ala Val Lys Glu Asn Lys Asp Asp
    1280                1285                1290

Leu Asn His Val Asp Leu Asn Val Cys Thr Ser Phe Ser Gly Pro
    1295                1300                1305

Gly Arg Ser Gly Met Ala Leu Met Glu Val Asn Leu Leu Ser Gly
    1310                1315                1320

Phe Met Val Pro Ser Glu Ala Ile Ser Leu Ser Glu Thr Val Lys
    1325                1330                1335

Lys Val Glu Tyr Asp His Gly Lys Leu Asn Leu Tyr Leu Asp Ser
    1340                1345                1350

Val Asn Glu Thr Gln Phe Cys Val Asn Ile Pro Ala Val Arg Asn
    1355                1360                1365

Phe Lys Val Ser Asn Thr Gln Asp Ala Ser Val Ser Ile Val Asp
    1370                1375                1380

Tyr Tyr Glu Pro Arg Arg Gln Ala Val Arg Ser Tyr Asn Ser Glu
    1385                1390                1395

Val Lys Leu Ser Ser Cys Asp Leu Cys Ser Asp Val Gln Gly Cys
    1400                1405                1410

Arg Pro Cys Glu Asp Gly Ala Ser Gly Ser His His His Ser Ser
    1415                1420                1425

Val Ile Phe Ile Phe Cys Phe Lys Leu Leu Tyr Phe Met Glu Leu
    1430                1435                1440

Trp Leu
    1445

<210> SEQ ID NO 3
<211> LENGTH: 4335
```

```
<212> TYPE: DNA
<213> ORGANISM: HUMAN
<220> FEATURE:
<221> NAME/KEY: CDS
<222> LOCATION: (1)..(4335)
<220> FEATURE:
<221> NAME/KEY: CDS
<222> LOCATION: (1)..(4335)

<400> SEQUENCE: 3 atg cag ggc cca ccg ctc ctg acc gcc gcc cac ctc ctc tgc gtg tgc      48
Met Gln Gly Pro Pro Leu Leu Thr Ala Ala His Leu Leu Cys Val Cys
1               5                   10                  15 acc gcc gcg ctg gcc gtg gct ccc ggg cct cgg ttt ctg gtg aca gcc      96
Thr Ala Ala Leu Ala Val Ala Pro Gly Pro Arg Phe Leu Val Thr Ala
                20                  25                  30 cca ggg atc atc agg ccc gga gga aat gtg act att ggg gtg gag ctt     144
Pro Gly Ile Ile Arg Pro Gly Gly Asn Val Thr Ile Gly Val Glu Leu
            35                  40                  45 ctg gaa cac tgc cct tca cag gtg act gtg aag gcg gag ctg ctc aag     192
Leu Glu His Cys Pro Ser Gln Val Thr Val Lys Ala Glu Leu Leu Lys
        50                  55                  60 aca gca tca aac ctc act gtc tct gtc ctg gaa gca gaa gga gtc ttt     240
Thr Ala Ser Asn Leu Thr Val Ser Val Leu Glu Ala Glu Gly Val Phe
65                  70                  75                  80 gaa aaa ggc tct ttt aag aca ctt act ctt cca tca cta cct ctg aac     288
Glu Lys Gly Ser Phe Lys Thr Leu Thr Leu Pro Ser Leu Pro Leu Asn
                85                  90                  95 agt gca gat gag att tat gag cta cgt gta acc gga cgt acc cag gat     336
Ser Ala Asp Glu Ile Tyr Glu Leu Arg Val Thr Gly Arg Thr Gln Asp
                100                 105                 110 gag att tta ttc tct aat agt acc cgc tta tca ttt gag acc aag aga     384
Glu Ile Leu Phe Ser Asn Ser Thr Arg Leu Ser Phe Glu Thr Lys Arg
            115                 120                 125 ata tct gtc ttc att caa aca gac aag gcc tta tac aag cca aag caa     432
Ile Ser Val Phe Ile Gln Thr Asp Lys Ala Leu Tyr Lys Pro Lys Gln
        130                 135                 140 gaa gtg aag ttt cgc att gtt aca ctc ttc tca gat ttt aag cct tac     480
Glu Val Lys Phe Arg Ile Val Thr Leu Phe Ser Asp Phe Lys Pro Tyr
145                 150                 155                 160 aaa acc tct tta aac att ctc att aag gac ccc aaa tca aat ttg atc     528
Lys Thr Ser Leu Asn Ile Leu Ile Lys Asp Pro Lys Ser Asn Leu Ile
                165                 170                 175 caa cag tgg ttg tca caa caa agt gat ctt gga gtc att tcc aaa act     576
Gln Gln Trp Leu Ser Gln Gln Ser Asp Leu Gly Val Ile Ser Lys Thr
                180                 185                 190 ttt cag cta tct tcc cat cca ata ctt ggt gac tgg tct att caa gtt     624
Phe Gln Leu Ser Ser His Pro Ile Leu Gly Asp Trp Ser Ile Gln Val
            195                 200                 205 caa gtg aat gac cag aca tat tat caa tca ttt cag gtt tca gaa tat     672
Gln Val Asn Asp Gln Thr Tyr Tyr Gln Ser Phe Gln Val Ser Glu Tyr
        210                 215                 220 gta tta cca aaa ttt gaa gtg act ttg cag aca cca tta tat tgt tct     720
Val Leu Pro Lys Phe Glu Val Thr Leu Gln Thr Pro Leu Tyr Cys Ser
225                 230                 235                 240 atg aat tct aag cat tta aat ggt acc atc acg gca aag tat aca tat     768
Met Asn Ser Lys His Leu Asn Gly Thr Ile Thr Ala Lys Tyr Thr Tyr
                245                 250                 255 ggg aag cca gtg aaa gga gac gta acg ctt aca ttt tta cct tta tcc     816
Gly Lys Pro Val Lys Gly Asp Val Thr Leu Thr Phe Leu Pro Leu Ser
                260                 265                 270
```

| | | |
|---|---|---|
| ttt tgg gga aag aag aaa aat att aca aaa aca ttt aag ata aat gga<br>Phe Trp Gly Lys Lys Lys Asn Ile Thr Lys Thr Phe Lys Ile Asn Gly<br>275                         280                       285 | | 864 |
| tct gca aac ttc tct ttt aat gat gaa gag atg aaa aat gta atg gat<br>Ser Ala Asn Phe Ser Phe Asn Asp Glu Glu Met Lys Asn Val Met Asp<br>     290                      295                     300 | | 912 |
| tct tca aat gga ctt tct gaa tac ctg gat cta tcc tcc cct gga cca<br>Ser Ser Asn Gly Leu Ser Glu Tyr Leu Asp Leu Ser Ser Pro Gly Pro<br>305                      310                     315                  320 | | 960 |
| gta gaa att tta acc aca gtg aca gaa tca gtt aca ggt att tca aga<br>Val Glu Ile Leu Thr Thr Val Thr Glu Ser Val Thr Gly Ile Ser Arg<br>               325                       330                  335 | | 1008 |
| aat gta agc act aat gtg ttc ttc aag caa cat gat tac atc att gag<br>Asn Val Ser Thr Asn Val Phe Phe Lys Gln His Asp Tyr Ile Ile Glu<br>            340                    345                   350 | | 1056 |
| ttt ttt gat tat act act gtc ttg aag cca tct ctc aac ttc aca gcc<br>Phe Phe Asp Tyr Thr Thr Val Leu Lys Pro Ser Leu Asn Phe Thr Ala<br>               355                     360                  365 | | 1104 |
| act gtg aag gta act cgt gct gat ggc aac caa ctg act ctt gaa gaa<br>Thr Val Lys Val Thr Arg Ala Asp Gly Asn Gln Leu Thr Leu Glu Glu<br>     370                      375                     380 | | 1152 |
| aga aga aat aat gta gtc ata aca gtg aca cag aga aac tat act gag<br>Arg Arg Asn Asn Val Val Ile Thr Val Thr Gln Arg Asn Tyr Thr Glu<br>385                         390                     395                  400 | | 1200 |
| tac tgg agc gga tct aac agt gga aat cag aaa atg gaa gct gtt cag<br>Tyr Trp Ser Gly Ser Asn Ser Gly Asn Gln Lys Met Glu Ala Val Gln<br>                    405                     410                  415 | | 1248 |
| aaa ata aat tat act gtc ccc caa agt gga act ttt aag att gaa ttc<br>Lys Ile Asn Tyr Thr Val Pro Gln Ser Gly Thr Phe Lys Ile Glu Phe<br>                   420                     425                  430 | | 1296 |
| cca atc ctg gag gat tcc agt gag cta cag ttg aag gcc tat ttc ctt<br>Pro Ile Leu Glu Asp Ser Ser Glu Leu Gln Leu Lys Ala Tyr Phe Leu<br>               435                    440                  445 | | 1344 |
| ggt agt aaa agt agc atg gca gtt cat agt ctg ttt aag tct cct agt<br>Gly Ser Lys Ser Ser Met Ala Val His Ser Leu Phe Lys Ser Pro Ser<br>           450                      455                   460 | | 1392 |
| aag aca tac atc caa cta aaa aca aga gat gaa aat ata aag gtg gga<br>Lys Thr Tyr Ile Gln Leu Lys Thr Arg Asp Glu Asn Ile Lys Val Gly<br>465                         470                     475                  480 | | 1440 |
| tcg cct ttt gag ttg gtg gtt agt ggc aac aaa cga ttg aag gag tta<br>Ser Pro Phe Glu Leu Val Val Ser Gly Asn Lys Arg Leu Lys Glu Leu<br>                   485                     490                  495 | | 1488 |
| agc tat atg gta gta tcc agg gga cag ttg gtg gct gta gga aaa caa<br>Ser Tyr Met Val Val Ser Arg Gly Gln Leu Val Ala Val Gly Lys Gln<br>                   500                     505                  510 | | 1536 |
| aat tca aca atg ttc tct tta aca cca gaa aat tct tgg act cca aaa<br>Asn Ser Thr Met Phe Ser Leu Thr Pro Glu Asn Ser Trp Thr Pro Lys<br>               515                     520                  525 | | 1584 |
| gcc tgt gta att gtg tat tat att gaa gat gat ggg gaa att ata agt<br>Ala Cys Val Ile Val Tyr Tyr Ile Glu Asp Asp Gly Glu Ile Ile Ser<br>     530                      535                     540 | | 1632 |
| gat gtt cta aaa att cct gtt cag ctt gtt ttt aaa aat aag ata aag<br>Asp Val Leu Lys Ile Pro Val Gln Leu Val Phe Lys Asn Lys Ile Lys<br>545                         550                     555                  560 | | 1680 |
| cta tat tgg agt aaa gtg aaa gct gaa cca tct gag aaa gtc tct ctt<br>Leu Tyr Trp Ser Lys Val Lys Ala Glu Pro Ser Glu Lys Val Ser Leu<br>                   565                     570                  575 | | 1728 |
| agg atc tct gtg aca cag cct gac tcc ata gtt ggg att gta gct gtt<br>Arg Ile Ser Val Thr Gln Pro Asp Ser Ile Val Gly Ile Val Ala Val<br>                   580                     585                  590 | | 1776 |

| | | |
|---|---|---|
| gac aaa agt gtg aat ctg atg aat gcc tct aat gat att aca atg gaa<br>Asp Lys Ser Val Asn Leu Met Asn Ala Ser Asn Asp Ile Thr Met Glu<br>595                 600               605 | | 1824 |
| aat gtg gtc cat gag ttg gaa ctt tat aac aca gga tat tat tta ggc<br>Asn Val Val His Glu Leu Glu Leu Tyr Asn Thr Gly Tyr Tyr Leu Gly<br>610                 615               620 | | 1872 |
| atg ttc atg aat tct ttt gca gtc ttt cag gaa tgt gga ctc tgg gta<br>Met Phe Met Asn Ser Phe Ala Val Phe Gln Glu Cys Gly Leu Trp Val<br>625                 630               635               640 | | 1920 |
| ttg aca gat gca aac ctc acg aag gat tat att gat ggt gtt tat gac<br>Leu Thr Asp Ala Asn Leu Thr Lys Asp Tyr Ile Asp Gly Val Tyr Asp<br>               645               650               655 | | 1968 |
| aat gca gaa tat gct gag agg ttt atg gag gaa aat gaa gga cat att<br>Asn Ala Glu Tyr Ala Glu Arg Phe Met Glu Glu Asn Glu Gly His Ile<br>               660               665               670 | | 2016 |
| gta gat att cat gac ttt tct ttg ggt agc agt cca cat gtc cga aag<br>Val Asp Ile His Asp Phe Ser Leu Gly Ser Ser Pro His Val Arg Lys<br>               675               680               685 | | 2064 |
| cat ttt cca gag act tgg att tgg cta gac acc aac atg ggt tcc agg<br>His Phe Pro Glu Thr Trp Ile Trp Leu Asp Thr Asn Met Gly Ser Arg<br>690                 695               700 | | 2112 |
| att tac caa gaa ttt gaa gta act gta cct gat tct atc act tct tgg<br>Ile Tyr Gln Glu Phe Glu Val Thr Val Pro Asp Ser Ile Thr Ser Trp<br>705                 710               715               720 | | 2160 |
| gtg gct act ggt ttt gtg atc tct gag gac ctg ggt ctt gga cta aca<br>Val Ala Thr Gly Phe Val Ile Ser Glu Asp Leu Gly Leu Gly Leu Thr<br>               725               730               735 | | 2208 |
| act act cca gtg gag ctc caa gcc ttc caa cca ttt ttc att ttt ttg<br>Thr Thr Pro Val Glu Leu Gln Ala Phe Gln Pro Phe Phe Ile Phe Leu<br>740                 745               750 | | 2256 |
| aat ctt ccc tac tct gtt atc aga ggt gaa gaa ttt gct ttg gaa ata<br>Asn Leu Pro Tyr Ser Val Ile Arg Gly Glu Glu Phe Ala Leu Glu Ile<br>               755               760               765 | | 2304 |
| act ata ttc aat tat ttg aaa gat gcc act gag gtt aag gta atc att<br>Thr Ile Phe Asn Tyr Leu Lys Asp Ala Thr Glu Val Lys Val Ile Ile<br>770                 775               780 | | 2352 |
| gag aaa agt gac aaa ttt gat att cta atg act tca aat gaa ata aat<br>Glu Lys Ser Asp Lys Phe Asp Ile Leu Met Thr Ser Asn Glu Ile Asn<br>785                 790               795               800 | | 2400 |
| gcc aca ggc cac cag cag acc ctt ctg gtt ccc agt gag gat ggg gca<br>Ala Thr Gly His Gln Gln Thr Leu Leu Val Pro Ser Glu Asp Gly Ala<br>               805               810               815 | | 2448 |
| act gtt ctt ttt ccc atc agg cca aca cat ctg gga gaa att cct atc<br>Thr Val Leu Phe Pro Ile Arg Pro Thr His Leu Gly Glu Ile Pro Ile<br>               820               825               830 | | 2496 |
| aca gtc aca gct ctt tca ccc act gct tct gat gct gtc acc cag atg<br>Thr Val Thr Ala Leu Ser Pro Thr Ala Ser Asp Ala Val Thr Gln Met<br>835                 840               845 | | 2544 |
| att tta gta aag gct gaa gga ata gaa aaa tca tat tca caa tcc atc<br>Ile Leu Val Lys Ala Glu Gly Ile Glu Lys Ser Tyr Ser Gln Ser Ile<br>850                 855               860 | | 2592 |
| tta tta gac ttg act gac aat agg cta cag agt acc ctg aaa act ttg<br>Leu Leu Asp Leu Thr Asp Asn Arg Leu Gln Ser Thr Leu Lys Thr Leu<br>865                 870               875               880 | | 2640 |
| agt ttc tca ttt cct cct aat aca gtg act ggc agt gaa aga gtt cag<br>Ser Phe Ser Phe Pro Pro Asn Thr Val Thr Gly Ser Glu Arg Val Gln<br>               885               890               895 | | 2688 |
| atc act gca att gga gat gtt ctt ggt cct tcc atc aat ggc tta gcc<br>Ile Thr Ala Ile Gly Asp Val Leu Gly Pro Ser Ile Asn Gly Leu Ala | | 2736 |

-continued

```
              900             905             910
tca ttg att cgg atg cct tat ggc tgt ggt gaa cag aac atg ata aat      2784
Ser Leu Ile Arg Met Pro Tyr Gly Cys Gly Glu Gln Asn Met Ile Asn
        915             920             925 ttt gct cca aat att tac att ttg gat tat ctg act aaa aag aaa caa      2832
Phe Ala Pro Asn Ile Tyr Ile Leu Asp Tyr Leu Thr Lys Lys Lys Gln
    930             935             940 ctg aca gat aat ttg aaa gaa aaa gct ctt tca ttt atg agg caa ggt      2880
Leu Thr Asp Asn Leu Lys Glu Lys Ala Leu Ser Phe Met Arg Gln Gly
945             950             955             960 tac cag aga gaa ctc ctc tat cag agg gaa gat ggc tct ttc agt gct      2928
Tyr Gln Arg Glu Leu Leu Tyr Gln Arg Glu Asp Gly Ser Phe Ser Ala
            965             970             975 ttt ggg aat tat gac cct tct ggg agc act tgg ttg tca gct ttt gtt      2976
Phe Gly Asn Tyr Asp Pro Ser Gly Ser Thr Trp Leu Ser Ala Phe Val
        980             985             990 tta aga tgt ttc ctt gaa gcc gat     cct tac ata gat att   gat cag aat      3024
Leu Arg Cys Phe Leu Glu Ala Asp     Pro Tyr Ile Asp Ile   Asp Gln Asn
            995             1000            1005 gtg tta cac aga aca tac act tgg ctt aaa gga cat cag aaa tcc      3069
Val Leu His Arg Thr Tyr Thr Trp Leu Lys Gly His Gln Lys Ser
    1010            1015            1020 aac ggt gaa ttt tgg gat cca gga aga gtg att cat agt gag ctt      3114
Asn Gly Glu Phe Trp Asp Pro Gly Arg Val Ile His Ser Glu Leu
    1025            1030            1035 caa ggt ggc aat aaa agt cca gta aca ctt aca gcc tat att gta      3159
Gln Gly Gly Asn Lys Ser Pro Val Thr Leu Thr Ala Tyr Ile Val
    1040            1045            1050 act tct ctc ctg gga tat aga aag tat cag cct aac att gat gtg      3204
Thr Ser Leu Leu Gly Tyr Arg Lys Tyr Gln Pro Asn Ile Asp Val
    1055            1060            1065 caa gag tct atc cat ttt ttg gag tct gaa ttc agt aga gga att      3249
Gln Glu Ser Ile His Phe Leu Glu Ser Glu Phe Ser Arg Gly Ile
    1070            1075            1080 tca gac aat tat act cta gcc ctt ata act tat gca ttg tca tca      3294
Ser Asp Asn Tyr Thr Leu Ala Leu Ile Thr Tyr Ala Leu Ser Ser
    1085            1090            1095 gtg ggg agt cct aaa gcg aag gaa gct ttg aat atg ctg act tgg      3339
Val Gly Ser Pro Lys Ala Lys Glu Ala Leu Asn Met Leu Thr Trp
    1100            1105            1110 aga gca gaa caa gaa ggt ggc atg caa ttc tgg gtg tca tca gag      3384
Arg Ala Glu Gln Glu Gly Gly Met Gln Phe Trp Val Ser Ser Glu
    1115            1120            1125 tcc aaa ctt tct gac tcc tgg cag cca cgc tcc ctg gat att gaa      3429
Ser Lys Leu Ser Asp Ser Trp Gln Pro Arg Ser Leu Asp Ile Glu
    1130            1135            1140 gtt gca gcc tat gca ctg ctc tca cac ttc tta caa ttt cag act      3474
Val Ala Ala Tyr Ala Leu Leu Ser His Phe Leu Gln Phe Gln Thr
    1145            1150            1155 tct gag gga atc cca att atg agg tgg cta agc agg caa aga aat      3519
Ser Glu Gly Ile Pro Ile Met Arg Trp Leu Ser Arg Gln Arg Asn
    1160            1165            1170 agc ttg ggt ggt ttt gca tct act cag gat acc act gtg gct tta      3564
Ser Leu Gly Gly Phe Ala Ser Thr Gln Asp Thr Thr Val Ala Leu
    1175            1180            1185 aag gct ctg tct gaa ttt gca gcc cta atg aat aca gaa agg aca      3609
Lys Ala Leu Ser Glu Phe Ala Ala Leu Met Asn Thr Glu Arg Thr
    1190            1195            1200 aat atc caa gtg acc gtg acg ggg cct agc tca cca agt cct gta      3654
```

-continued

| | | | | | | | | | | | | | | |
|---|---|---|---|---|---|---|---|---|---|---|---|---|---|---|
| Asn | Ile | Gln | Val | Thr | Val | Thr | Gly | Pro | Ser | Ser | Pro | Ser | Pro | Val |
| | 1205 | | | | 1210 | | | | 1215 | | | | | |

```
aag ttt ctg att gac aca cac aac cgc tta ctc ctt cag aca gca      3699
Lys Phe Leu Ile Asp Thr His Asn Arg Leu Leu Leu Gln Thr Ala
    1220                1225                1230 gag ctt gct gtg gta cag cca atg gca gtt aat att tcc gca aat      3744
Glu Leu Ala Val Val Gln Pro Met Ala Val Asn Ile Ser Ala Asn
1235                1240                1245 ggt ttt gga ttt gct att tgt cag ctc aat gtt gta tat aat gtg      3789
Gly Phe Gly Phe Ala Ile Cys Gln Leu Asn Val Val Tyr Asn Val
    1250                1255                1260 aag gct tct ggg tct tct aga aga cga aga tct atc caa aat caa      3834
Lys Ala Ser Gly Ser Ser Arg Arg Arg Arg Ser Ile Gln Asn Gln
1265                1270                1275 gaa gcc ttt gat tta gat gtt gct gta aaa gaa aat aaa gat gat      3879
Glu Ala Phe Asp Leu Asp Val Ala Val Lys Glu Asn Lys Asp Asp
    1280                1285                1290 ctc aat cat gtg gat ttg aat gtg tgt aca agc ttt tcg ggc ccg      3924
Leu Asn His Val Asp Leu Asn Val Cys Thr Ser Phe Ser Gly Pro
1295                1300                1305 ggt agg agt ggc atg gct ctt atg gaa gtt aac cta tta agt ggc      3969
Gly Arg Ser Gly Met Ala Leu Met Glu Val Asn Leu Leu Ser Gly
    1310                1315                1320 ttt atg gtg cct tca gaa gca att tct ctg agc gag aca gtg aag      4014
Phe Met Val Pro Ser Glu Ala Ile Ser Leu Ser Glu Thr Val Lys
1325                1330                1335 aaa gtg gaa tat gat cat gga aaa ctc aac ctc tat tta gat tct      4059
Lys Val Glu Tyr Asp His Gly Lys Leu Asn Leu Tyr Leu Asp Ser
    1340                1345                1350 gta aat gaa acc cag ttt tgt gtt aat att cct gct gtg aga aac      4104
Val Asn Glu Thr Gln Phe Cys Val Asn Ile Pro Ala Val Arg Asn
1355                1360                1365 ttt aaa gtt tca aat acc caa gat gct tca gtg tcc ata gtg gat      4149
Phe Lys Val Ser Asn Thr Gln Asp Ala Ser Val Ser Ile Val Asp
    1370                1375                1380 tac tat gag cca agg aga cag gcg gtg aga agt tac aac tct gaa      4194
Tyr Tyr Glu Pro Arg Arg Gln Ala Val Arg Ser Tyr Asn Ser Glu
1385                1390                1395 gtg aag ctg tcc tcc tgt gac ctt tgc agt gat gtc cag ggc tgc      4239
Val Lys Leu Ser Ser Cys Asp Leu Cys Ser Asp Val Gln Gly Cys
    1400                1405                1410 cgt cct tgt gag gat gga gct tca ggc tcc cat cat cac tct tca      4284
Arg Pro Cys Glu Asp Gly Ala Ser Gly Ser His His His Ser Ser
1415                1420                1425 gtc att ttt att ttc tgt ttc aag ctt ctg tac ttt atg gaa ctt      4329
Val Ile Phe Ile Phe Cys Phe Lys Leu Leu Tyr Phe Met Glu Leu
    1430                1435                1440 tgg ctg                                                          4335
Trp Leu
    1445
```

<210> SEQ ID NO 4
<211> LENGTH: 1445
<212> TYPE: PRT
<213> ORGANISM: HUMAN

<400> SEQUENCE: 4

Met Gln Gly Pro Pro Leu Leu Thr Ala Ala His Leu Leu Cys Val Cys
1               5                   10                  15

Thr Ala Ala Leu Ala Val Ala Pro Gly Pro Arg Phe Leu Val Thr Ala

-continued

```
                    20                  25                  30
Pro Gly Ile Ile Arg Pro Gly Asn Val Thr Ile Gly Val Glu Leu
                35                  40                  45
Leu Glu His Cys Pro Ser Gln Val Thr Val Lys Ala Glu Leu Leu Lys
 50                  55                  60
Thr Ala Ser Asn Leu Thr Val Ser Val Leu Glu Ala Glu Gly Val Phe
 65                  70                  75                  80
Glu Lys Gly Ser Phe Lys Thr Leu Thr Leu Pro Ser Leu Pro Leu Asn
                 85                  90                  95
Ser Ala Asp Glu Ile Tyr Glu Leu Arg Val Thr Gly Arg Thr Gln Asp
                100                 105                 110
Glu Ile Leu Phe Ser Asn Ser Thr Arg Leu Ser Phe Glu Thr Lys Arg
                115                 120                 125
Ile Ser Val Phe Ile Gln Thr Asp Lys Ala Leu Tyr Lys Pro Lys Gln
                130                 135                 140
Glu Val Lys Phe Arg Ile Val Thr Leu Phe Ser Asp Phe Lys Pro Tyr
145                 150                 155                 160
Lys Thr Ser Leu Asn Ile Leu Ile Lys Asp Pro Lys Ser Asn Leu Ile
                165                 170                 175
Gln Gln Trp Leu Ser Gln Ser Asp Leu Gly Val Ile Ser Lys Thr
                180                 185                 190
Phe Gln Leu Ser Ser His Pro Ile Leu Gly Asp Trp Ser Ile Gln Val
                195                 200                 205
Gln Val Asn Asp Gln Thr Tyr Tyr Gln Ser Phe Gln Val Ser Glu Tyr
                210                 215                 220
Val Leu Pro Lys Phe Glu Val Thr Leu Gln Thr Pro Leu Tyr Cys Ser
225                 230                 235                 240
Met Asn Ser Lys His Leu Asn Gly Thr Ile Thr Ala Lys Tyr Thr Tyr
                245                 250                 255
Gly Lys Pro Val Lys Gly Asp Val Thr Leu Thr Phe Leu Pro Leu Ser
                260                 265                 270
Phe Trp Gly Lys Lys Asn Ile Thr Lys Thr Phe Lys Ile Asn Gly
                275                 280                 285
Ser Ala Asn Phe Ser Phe Asn Asp Glu Glu Met Lys Asn Val Met Asp
                290                 295                 300
Ser Ser Asn Gly Leu Ser Glu Tyr Leu Asp Leu Ser Ser Pro Gly Pro
305                 310                 315                 320
Val Glu Ile Leu Thr Thr Val Thr Glu Ser Val Thr Gly Ile Ser Arg
                325                 330                 335
Asn Val Ser Thr Asn Val Phe Phe Lys Gln His Asp Tyr Ile Ile Glu
                340                 345                 350
Phe Phe Asp Tyr Thr Thr Val Leu Lys Pro Ser Leu Asn Phe Thr Ala
                355                 360                 365
Thr Val Lys Val Thr Arg Ala Asp Gly Asn Gln Leu Thr Leu Glu Glu
                370                 375                 380
Arg Arg Asn Asn Val Val Ile Thr Val Thr Gln Arg Asn Tyr Thr Glu
385                 390                 395                 400
Tyr Trp Ser Gly Ser Asn Ser Gly Asn Gln Lys Met Glu Ala Val Gln
                405                 410                 415
Lys Ile Asn Tyr Thr Val Pro Gln Ser Gly Thr Phe Lys Ile Glu Phe
                420                 425                 430
Pro Ile Leu Glu Asp Ser Ser Glu Leu Gln Leu Lys Ala Tyr Phe Leu
                435                 440                 445
```

```
Gly Ser Lys Ser Ser Met Ala Val His Ser Leu Phe Lys Ser Pro Ser
    450                 455                 460

Lys Thr Tyr Ile Gln Leu Lys Thr Arg Asp Glu Asn Ile Lys Val Gly
465                 470                 475                 480

Ser Pro Phe Glu Leu Val Val Ser Gly Asn Lys Arg Leu Lys Glu Leu
                485                 490                 495

Ser Tyr Met Val Val Ser Arg Gly Gln Leu Val Ala Val Gly Lys Gln
                500                 505                 510

Asn Ser Thr Met Phe Ser Leu Thr Pro Glu Asn Ser Trp Thr Pro Lys
            515                 520                 525

Ala Cys Val Ile Val Tyr Tyr Ile Glu Asp Gly Glu Ile Ile Ser
        530                 535                 540

Asp Val Leu Lys Ile Pro Val Gln Leu Val Phe Lys Asn Lys Ile Lys
545                 550                 555                 560

Leu Tyr Trp Ser Lys Val Lys Ala Glu Pro Ser Glu Lys Val Ser Leu
                565                 570                 575

Arg Ile Ser Val Thr Gln Pro Asp Ser Ile Val Gly Ile Val Ala Val
                580                 585                 590

Asp Lys Ser Val Asn Leu Met Asn Ala Ser Asn Asp Ile Thr Met Glu
            595                 600                 605

Asn Val Val His Glu Leu Glu Leu Tyr Asn Thr Gly Tyr Tyr Leu Gly
            610                 615                 620

Met Phe Met Asn Ser Phe Ala Val Phe Gln Glu Cys Gly Leu Trp Val
625                 630                 635                 640

Leu Thr Asp Ala Asn Leu Thr Lys Asp Tyr Ile Asp Gly Val Tyr Asp
                645                 650                 655

Asn Ala Glu Tyr Ala Glu Arg Phe Met Glu Asn Glu Gly His Ile
                660                 665                 670

Val Asp Ile His Asp Phe Ser Leu Gly Ser Ser Pro His Val Arg Lys
            675                 680                 685

His Phe Pro Glu Thr Trp Ile Trp Leu Asp Thr Asn Met Gly Ser Arg
    690                 695                 700

Ile Tyr Gln Glu Phe Glu Val Thr Val Pro Asp Ser Ile Thr Ser Trp
705                 710                 715                 720

Val Ala Thr Gly Phe Val Ile Ser Glu Asp Leu Gly Leu Gly Leu Thr
                725                 730                 735

Thr Thr Pro Val Glu Leu Gln Ala Phe Gln Pro Phe Ile Phe Leu
                740                 745                 750

Asn Leu Pro Tyr Ser Val Ile Arg Gly Glu Glu Phe Ala Leu Glu Ile
            755                 760                 765

Thr Ile Phe Asn Tyr Leu Lys Asp Ala Thr Glu Val Lys Val Ile Ile
        770                 775                 780

Glu Lys Ser Asp Lys Phe Asp Ile Leu Met Thr Ser Asn Glu Ile Asn
785                 790                 795                 800

Ala Thr Gly His Gln Gln Thr Leu Leu Val Pro Ser Glu Asp Gly Ala
                805                 810                 815

Thr Val Leu Phe Pro Ile Arg Pro Thr His Leu Gly Glu Ile Pro Ile
                820                 825                 830

Thr Val Thr Ala Leu Ser Pro Thr Ala Ser Asp Ala Val Thr Gln Met
            835                 840                 845

Ile Leu Val Lys Ala Glu Gly Ile Glu Lys Ser Tyr Ser Gln Ser Ile
        850                 855                 860
```

-continued

```
Leu Leu Asp Leu Thr Asp Asn Arg Leu Gln Ser Thr Leu Lys Thr Leu
865                 870                 875                 880

Ser Phe Ser Phe Pro Pro Asn Thr Val Thr Gly Ser Glu Arg Val Gln
                885                 890                 895

Ile Thr Ala Ile Gly Asp Val Leu Gly Pro Ser Ile Asn Gly Leu Ala
            900                 905                 910

Ser Leu Ile Arg Met Pro Tyr Gly Cys Gly Glu Gln Asn Met Ile Asn
        915                 920                 925

Phe Ala Pro Asn Ile Tyr Ile Leu Asp Tyr Leu Thr Lys Lys Gln
    930                 935                 940

Leu Thr Asp Asn Leu Lys Glu Lys Ala Leu Ser Phe Met Arg Gln Gly
945                 950                 955                 960

Tyr Gln Arg Glu Leu Leu Tyr Gln Arg Glu Asp Gly Ser Phe Ser Ala
                965                 970                 975

Phe Gly Asn Tyr Asp Pro Ser Gly Ser Thr Trp Leu Ser Ala Phe Val
            980                 985                 990

Leu Arg Cys Phe Leu Glu Ala Asp Pro Tyr Ile Asp Ile Asp Gln Asn
        995                 1000                1005

Val Leu His Arg Thr Tyr Thr Trp Leu Lys Gly His Gln Lys Ser
    1010                1015                1020

Asn Gly Glu Phe Trp Asp Pro Gly Arg Val Ile His Ser Glu Leu
    1025                1030                1035

Gln Gly Gly Asn Lys Ser Pro Val Thr Leu Thr Ala Tyr Ile Val
    1040                1045                1050

Thr Ser Leu Leu Gly Tyr Arg Lys Tyr Gln Pro Asn Ile Asp Val
    1055                1060                1065

Gln Glu Ser Ile His Phe Leu Glu Ser Glu Phe Ser Arg Gly Ile
    1070                1075                1080

Ser Asp Asn Tyr Thr Leu Ala Leu Ile Thr Tyr Ala Leu Ser Ser
    1085                1090                1095

Val Gly Ser Pro Lys Ala Lys Glu Ala Leu Asn Met Leu Thr Trp
    1100                1105                1110

Arg Ala Glu Gln Glu Gly Gly Met Gln Phe Trp Val Ser Ser Glu
    1115                1120                1125

Ser Lys Leu Ser Asp Ser Trp Gln Pro Arg Ser Leu Asp Ile Glu
    1130                1135                1140

Val Ala Ala Tyr Ala Leu Leu Ser His Phe Leu Gln Phe Gln Thr
    1145                1150                1155

Ser Glu Gly Ile Pro Ile Met Arg Trp Leu Ser Arg Gln Arg Asn
    1160                1165                1170

Ser Leu Gly Gly Phe Ala Ser Thr Gln Asp Thr Thr Val Ala Leu
    1175                1180                1185

Lys Ala Leu Ser Glu Phe Ala Ala Leu Met Asn Thr Glu Arg Thr
    1190                1195                1200

Asn Ile Gln Val Thr Val Thr Gly Pro Ser Ser Pro Ser Pro Val
    1205                1210                1215

Lys Phe Leu Ile Asp Thr His Asn Arg Leu Leu Leu Gln Thr Ala
    1220                1225                1230

Glu Leu Ala Val Val Gln Pro Met Ala Val Asn Ile Ser Ala Asn
    1235                1240                1245

Gly Phe Gly Phe Ala Ile Cys Gln Leu Asn Val Val Tyr Asn Val
    1250                1255                1260

Lys Ala Ser Gly Ser Ser Arg Arg Arg Arg Ser Ile Gln Asn Gln
```

-continued

|   |   |   |   | 1265 |   |   |   |   | 1270 |   |   |   |   | 1275 |
|---|---|---|---|------|---|---|---|---|------|---|---|---|---|------|
| Glu | Ala | Phe | Asp | Leu | Asp | Val | Ala | Val | Lys | Glu | Asn | Lys | Asp | Asp |
|   |   |   |   | 1280 |   |   |   |   | 1285 |   |   |   |   | 1290 |
| Leu | Asn | His | Val | Asp | Leu | Asn | Val | Cys | Thr | Ser | Phe | Ser | Gly | Pro |
|   |   |   |   | 1295 |   |   |   |   | 1300 |   |   |   |   | 1305 |
| Gly | Arg | Ser | Gly | Met | Ala | Leu | Met | Glu | Val | Asn | Leu | Leu | Ser | Gly |
|   |   |   |   | 1310 |   |   |   |   | 1315 |   |   |   |   | 1320 |
| Phe | Met | Val | Pro | Ser | Glu | Ala | Ile | Ser | Leu | Ser | Glu | Thr | Val | Lys |
|   |   |   |   | 1325 |   |   |   |   | 1330 |   |   |   |   | 1335 |
| Lys | Val | Glu | Tyr | Asp | His | Gly | Lys | Leu | Asn | Leu | Tyr | Leu | Asp | Ser |
|   |   |   |   | 1340 |   |   |   |   | 1345 |   |   |   |   | 1350 |
| Val | Asn | Glu | Thr | Gln | Phe | Cys | Val | Asn | Ile | Pro | Ala | Val | Arg | Asn |
|   |   |   |   | 1355 |   |   |   |   | 1360 |   |   |   |   | 1365 |
| Phe | Lys | Val | Ser | Asn | Thr | Gln | Asp | Ala | Ser | Val | Ser | Ile | Val | Asp |
|   |   |   |   | 1370 |   |   |   |   | 1375 |   |   |   |   | 1380 |
| Tyr | Tyr | Glu | Pro | Arg | Arg | Gln | Ala | Val | Arg | Ser | Tyr | Asn | Ser | Glu |
|   |   |   |   | 1385 |   |   |   |   | 1390 |   |   |   |   | 1395 |
| Val | Lys | Leu | Ser | Ser | Cys | Asp | Leu | Cys | Ser | Asp | Val | Gln | Gly | Cys |
|   |   |   |   | 1400 |   |   |   |   | 1405 |   |   |   |   | 1410 |
| Arg | Pro | Cys | Glu | Asp | Gly | Ala | Ser | Gly | Ser | His | His | His | Ser | Ser |
|   |   |   |   | 1415 |   |   |   |   | 1420 |   |   |   |   | 1425 |
| Val | Ile | Phe | Ile | Phe | Cys | Phe | Lys | Leu | Leu | Tyr | Phe | Met | Glu | Leu |
|   |   |   |   | 1430 |   |   |   |   | 1435 |   |   |   |   | 1440 |
| Trp | Leu |
|   |   |
| 1445 |   |

<210> SEQ ID NO 5
<211> LENGTH: 2608
<212> TYPE: DNA
<213> ORGANISM: HUMAN
<220> FEATURE:
<221> NAME/KEY: Intron
<222> LOCATION: (1)..(951)
<220> FEATURE:
<221> NAME/KEY: exon
<222> LOCATION: (952)..(1069)
<220> FEATURE:
<221> NAME/KEY: Intron
<222> LOCATION: (1070)..(2608)

<400> SEQUENCE: 5

| gtaaaaattt | ataaagttct | ttgcccatac | atattttgtt | tagtgtttgt | tttaaataag | 60 |
| ctttgcccgc | tttctaatgt | ttaagtacaa | acatagtgta | actaagaact | aagtagacca | 120 |
| aaaggatttt | ttaggaaatg | atattttattg | aatctaaata | cagttttttga | taaagccaca | 180 |
| cataaattat | ggcaggaagg | tctcatcaat | gagaagatag | gccttttttt | tttttttttaa | 240 |
| ctgaagggtg | attttgactt | ccttgaagtc | tcatgattct | tgttgaagaa | aaattgctgg | 300 |
| gagtacattt | gttgtcacag | gatgggaagc | actcatgatt | acctcctgtg | accccctggca | 360 |
| gtgctgctaa | ctgaaccctg | ctcctcacaa | agcattccca | ggagtcacag | ggagaagggg | 420 |
| catgggtggt | ggaaagaatt | cagcttggct | gataaacccc | gtaccacctg | gcctgataat | 480 |
| tgagcaggta | aatcatgaaa | tccacatagt | attttatagt | cagctgttta | aagatacttg | 540 |
| agttaacaca | tgagtgaaat | ctcaaggaaa | caaataacag | cattgacagg | gatacagaga | 600 |
| aaaacttctg | caaatttaga | gaaaaaattg | gagttaagtt | tgaaaatgtg | tatttattat | 660 |
| ctataaaaaa | tttgtgaaaa | aataatgttt | attctgaaga | tgtaaatttt | gcaggaagat | 720 |

-continued

```
tttattagaa tatggatcaa tatgcagtat tatgacccta tgatgaccta ttctttgaaa      780
agttgggatt tactgtttta tacttaaacc ttttaaatgg ttttaaattc agatatgtaa      840
acaataggaa aaattgaaat tcttccaaaa atagtttaga ttattttggc ttatttcaaa      900
atgtatcagt tcttggtttt gtgatgttta tatttattat cttgacttca gt tac agg     958
                                                          Tyr Arg
                                                            1 att tac caa gaa ttt gaa gta act gta cct gat tct atc act tct tgg      1006
Ile Tyr Gln Glu Phe Glu Val Thr Val Pro Asp Ser Ile Thr Ser Trp
      5                  10                  15 gtg gct act ggt ttt gtg atc tct gag gac ctg ggt ctt gga cta aca      1054
Val Ala Thr Gly Phe Val Ile Ser Glu Asp Leu Gly Leu Gly Leu Thr
 20                  25                  30 act act cca gtg gag gtattgtatt aaagagctgc ttatcagtat tacggtgaca      1109
Thr Thr Pro Val Glu
35 ttaagctaat acagcgtcag ctcctcaatt ttttttttaa atgactgctt ataatgttta    1169 tcacagttta gagattcctt ggctttgtct ttaggttttt atctgtttta tatttaagaa    1229 tgtgagctat atatagctat ataaactgct aaatgtgcaa agtccgtatt aagatttggg    1289 tagaaaagtt tattattgac ctgaactaac catctccaaa ggccagaaga gagagaaaga    1349 aaagagaga gagagaaaga ggagaggaga gagagagtga gtctttctat ttgtcctctt     1409 caagaatgaa cagaacttct caagatgttc cctagccaat attccatcat gtcttttggt    1469 caaattgcat catatattgt ttcctaagcc agtcactggc aggaggaata taatgaccat    1529 gagtggcctg aattttctca tttgaaattg aaatgtaatt ttgatttaca aaataatcgt    1589 attcatgaaa aatacagtgt agattgaaaa atgctttggg tttatataga aattggaatt    1649 agattgtaag ctcaggccac tataaacaga caattcagca acatgaatgt ctgaagggac    1709 attcaagaat cattaggaac atggggcaat ttttcattgt ctggggctgt cctgagtatt    1769 gcagactgtc acccactaac tacctatagc accttcgagt catggtgaca atctaagaca    1829 ccttcacaaa tgtgcagata aactctgag ggagttactg ctgccagcaa aaccactggc    1889 ctaaactaac ccaggtttag ctttagatgc aggtgtgggg cttggccttt tctgtaggac    1949 ttggccaaca atatcagaat tgggtcactg aggaggaagc acatgtattc agatgtccca    2009 cacattttct catctgtatg taaaaataaa tcatatatat gttttagaaa taatttccaa    2069 tttcctcttt aaatttagtc aggaagcaca tgtattcaga tgtcccacac tagaacaggg    2129 gctgttggat ttggcagggc ttttaaagca gattggtgga gtcaatacag catgaaagaa    2189 gagcaaattg cttcgggatt agacaggctg ggttctagtt ctggctcctc tacttgccag    2249 caatatgaat ttgtactagt tacaaaaatc tcaaaaattt aattttcttt tctataaact    2309 aggagactaa cagtaacctt atggggttgt aataaccaaa caaaataatt tatgtgaagt    2369 gtttggttgc tataaggcac ttaataaagt atagcaatta ttatgttaag taacataaat    2429 caagtcaatt tgccgtcatt catttgtgat aagttgctgt ttgctttctg ttgatagcaa    2489 gttgacattt ctagctgaag ttaaaagctt cacaggtttt ataaagattg catttaattg    2549 cataaaatgt gaagaatttt gacctgaata aaaatatgta ctcgttgtgt tctttccag     2608
```

<210> SEQ ID NO 6
<211> LENGTH: 23
<212> TYPE: DNA
<213> ORGANISM: HUMAN

<400> SEQUENCE: 6
ttcaaattct tggtaaatcc tgt                23

<210> SEQ ID NO 7
<211> LENGTH: 23
<212> TYPE: DNA
<213> ORGANISM: HUMAN

<400> SEQUENCE: 7
ttcaaattct tggtaaatcc tgg                23

<210> SEQ ID NO 8
<211> LENGTH: 22
<212> TYPE: DNA
<213> ORGANISM: HUMAN

<400> SEQUENCE: 8
atgaccttat gatgacctat tc                 22

<210> SEQ ID NO 9
<211> LENGTH: 18
<212> TYPE: DNA
<213> ORGANISM: HUMAN

<400> SEQUENCE: 9
tttagattat tttggctt                      18

<210> SEQ ID NO 10
<211> LENGTH: 18
<212> TYPE: DNA
<213> ORGANISM: HUMAN

<400> SEQUENCE: 10
atggttagtt caggtcaa                      18

<210> SEQ ID NO 11
<211> LENGTH: 27
<212> TYPE: DNA
<213> ORGANISM: HUMAN

<400> SEQUENCE: 11
tgtatcagtt cttggttttg tgatgtt            27

<210> SEQ ID NO 12
<211> LENGTH: 30
<212> TYPE: DNA
<213> ORGANISM: HUMAN

<400> SEQUENCE: 12
ccaagaagtg atagaatcag gtacagttac         30

<210> SEQ ID NO 13
<211> LENGTH: 40
<212> TYPE: DNA
<213> ORGANISM: HUMAN

<400> SEQUENCE: 13
tattatcttg acttcagtta caggatttac caagaatttg    40

<210> SEQ ID NO 14
<211> LENGTH: 37
<212> TYPE: DNA
<213> ORGANISM: HUMAN

```
<400> SEQUENCE: 14
tattatcttg acttcagttc caggatttac caagaat                                37

<210> SEQ ID NO 15
<211> LENGTH: 18
<212> TYPE: DNA
<213> ORGANISM: synthetic construct
<220> FEATURE:
<221> NAME/KEY: primer
<222> LOCATION: (1)..(18)

<400> SEQUENCE: 15
gtagcccagg cagacgcc                                                     18

<210> SEQ ID NO 16
<211> LENGTH: 20
<212> TYPE: DNA
<213> ORGANISM: synthetic construct
<220> FEATURE:
<221> NAME/KEY: primer
<222> LOCATION: (1)..(20)

<400> SEQUENCE: 16
cgcattgtta cactcttctc                                                   20

<210> SEQ ID NO 17
<211> LENGTH: 19
<212> TYPE: DNA
<213> ORGANISM: synthetic construct
<220> FEATURE:
<221> NAME/KEY: primer
<222> LOCATION: (1)..(19)

<400> SEQUENCE: 17
gattcttcaa atggactttt                                                   19

<210> SEQ ID NO 18
<211> LENGTH: 21
<212> TYPE: DNA
<213> ORGANISM: synthetic construct
<220> FEATURE:
<221> NAME/KEY: primer
<222> LOCATION: (1)..(21)

<400> SEQUENCE: 18
tgaattccca atcctggagg a                                                 21

<210> SEQ ID NO 19
<211> LENGTH: 20
<212> TYPE: DNA
<213> ORGANISM: synthetic construct
<220> FEATURE:
<221> NAME/KEY: primer
<222> LOCATION: (1)..(20)

<400> SEQUENCE: 19
ttcaggaatg tggactctgg                                                   20

<210> SEQ ID NO 20
<211> LENGTH: 20
<212> TYPE: DNA
<213> ORGANISM: synthetic construct
<220> FEATURE:
<221> NAME/KEY: primer
<222> LOCATION: (1)..(20)

<400> SEQUENCE: 20
```
ctgggagcac ttggttgtca                                           20

<210> SEQ ID NO 21
<211> LENGTH: 20
<212> TYPE: DNA
<213> ORGANISM: synthetic construct
<220> FEATURE:
<221> NAME/KEY: primer
<222> LOCATION: (1)..(20)

<400> SEQUENCE: 21
acaatttcag acttctgagg                                           20

<210> SEQ ID NO 22
<211> LENGTH: 21
<212> TYPE: DNA
<213> ORGANISM: synthetic construct
<220> FEATURE:
<221> NAME/KEY: primer
<222> LOCATION: (1)..(21)

<400> SEQUENCE: 22
gacgaagatc tatccaaaat c                                         21

<210> SEQ ID NO 23
<211> LENGTH: 22
<212> TYPE: DNA
<213> ORGANISM: synthetic construct
<220> FEATURE:
<221> NAME/KEY: primer
<222> LOCATION: (1)..(22)

<400> SEQUENCE: 23
gtgacaacca ctgttggatc aa                                        22

<210> SEQ ID NO 24
<211> LENGTH: 20
<212> TYPE: DNA
<213> ORGANISM: synthetic construct
<220> FEATURE:
<221> NAME/KEY: primer
<222> LOCATION: (1)..(20)

<400> SEQUENCE: 24
tacatttctt gaaatacctg                                           20

<210> SEQ ID NO 25
<211> LENGTH: 18
<212> TYPE: DNA
<213> ORGANISM: synthetic construct
<220> FEATURE:
<221> NAME/KEY: primer
<222> LOCATION: (1)..(18)

<400> SEQUENCE: 25
ggctgtgtca cagagatc                                             18

<210> SEQ ID NO 26
<211> LENGTH: 20
<212> TYPE: DNA
<213> ORGANISM: synthetic construct
<220> FEATURE:
<221> NAME/KEY: primer
<222> LOCATION: (1)..(20)

<400> SEQUENCE: 26

-continued gccacccaag aagtgataga 20

<210> SEQ ID NO 27
<211> LENGTH: 19
<212> TYPE: DNA
<213> ORGANISM: synthetic construct
<220> FEATURE:
<221> NAME/KEY: primer
<222> LOCATION: (1)..(19)

<400> SEQUENCE: 27
cggcttcaag gaaacatct 19

<210> SEQ ID NO 28
<211> LENGTH: 22
<212> TYPE: DNA
<213> ORGANISM: synthetic construct
<220> FEATURE:
<221> NAME/KEY: primer
<222> LOCATION: (1)..(22)

<400> SEQUENCE: 28
cagcaacatc taaatcaaag gc 22

<210> SEQ ID NO 29
<211> LENGTH: 18
<212> TYPE: DNA
<213> ORGANISM: synthetic construct
<220> FEATURE:
<221> NAME/KEY: primer
<222> LOCATION: (1)..(18)

<400> SEQUENCE: 29
cacagccaaa gttccata 18

<210> SEQ ID NO 30
<211> LENGTH: 20
<212> TYPE: DNA
<213> ORGANISM: synthetic construct
<220> FEATURE:
<221> NAME/KEY: primer
<222> LOCATION: (1)..(20)

<400> SEQUENCE: 30
gctaggacct gttgtacacc 20